United States Patent
Chuang et al.

(10) Patent No.: US 10,723,791 B2
(45) Date of Patent: Jul. 28, 2020

(54) COMPOSITIONS OF ISOLATED MONOCLONAL ANTIBODIES AND/OR ANTIGEN-BINDING FRAGMENTS THEREOF AGAINST INDOXYL SULFATE AND USES THEREOF

(71) Applicant: LEADGENE BIOMEDICAL, INC., Tainan (TW)

(72) Inventors: Yung-Chun Chuang, Tainan (TW); Yu-Wei Cheng, Tainan (TW); Chih-Hui Kao, Tainan (TW)

(73) Assignee: LEADGENE BIOMEDICAL, INC., Tainan (TW)

( * ) Notice: Subject to any disclaimer, the term of this patent is extended or adjusted under 35 U.S.C. 154(b) by 0 days.

(21) Appl. No.: 16/388,622

(22) Filed: Apr. 18, 2019

(65) Prior Publication Data
US 2020/0031909 A1    Jan. 30, 2020

Related U.S. Application Data

(60) Provisional application No. 62/659,256, filed on Apr. 18, 2018.

(51) Int. Cl.
| | | |
|---|---|---|
| C07K 16/18 | (2006.01) | |
| A61P 39/00 | (2006.01) | |
| A61P 13/12 | (2006.01) | |
| A61K 39/395 | (2006.01) | |
| G01N 33/53 | (2006.01) | |
| G01N 33/68 | (2006.01) | |
| A61K 39/00 | (2006.01) | |

(52) U.S. Cl.
CPC .............. *C07K 16/18* (2013.01); *A61P 39/00* (2018.01); *G01N 33/5308* (2013.01); *A61K 2039/505* (2013.01)

(58) Field of Classification Search
CPC .............. C07K 16/18; G01N 33/5308; G01N 33/6812; G01N 2800/347; A61P 39/00; A61P 13/12; A61K 2039/505; A61K 39/395
See application file for complete search history.

(56) References Cited

U.S. PATENT DOCUMENTS

| | | | |
|---|---|---|---|
| 8,206,591 B2 | 6/2012 | Kotanko et al. | |
| 2015/0355171 A1* | 12/2015 | Hoshi | C07K 16/44 435/7.93 |

FOREIGN PATENT DOCUMENTS

EP    2957911 A1    12/2015

OTHER PUBLICATIONS

Meyer, T. W., and T. H. Hostetter. 2007. Uremia. N. Engl. J. Med. 357: 1316-1325.
Vanholder, R., R. De Smet, and N. Lameire. 2001. Protein-bound uremic solutes: the forgotten toxins. Kidney Int. Suppl. 78: S266-270.
Lee, C.-T., C.-C. Kuo, Y.-M. Chen, C.-Y. Hsu, W.-C. Lee, Y.-C. Tsai, H.-Y. Ng, L.-C. Kuo, T. T.-Y. Chiou, Y.-K. Yang, B.-C. Cheng, and J.-B. Chen. 2010. Factors associated with blood concentrations of indoxyl sulfate and p-cresol in patients undergoing peritoneal dialysis. Perit. Dial. Int. J. Int. Soc. Perit. Dial. 30: 456-463.
Wu, I.-W., K.-H. Hsu, C.-C. Lee, C.-Y. Sun, H.-J. Hsu, C.-J. Tsai, C.-Y. Tzen, Y.-C. Wang, C.-Y. Lin, and M.-S. Wu. 2011. p-Cresyl sulphate and indoxyl sulphate predict progression of chronic kidney disease. Nephrol. Dial. Transplant. Off. Publ. Eur. Dial. Transpl. Assoc.—Eur. Ren. Assoc. 26: 938-947.
Schulman, G., T. Berl, G. J. Beck, G. Remuzzi, E Ritz, K. Arita, A. Kato, and M. Shimizu. 2015. Randomized Placebo-Controlled EPPIC Trials of AST-120 in CKD. J. Am. Soc. Nephrol. JASN 26: 1732-1746.
Yamaguchi, J., T. Tanaka, and R. Inagi. 2017. Effect of AST-120 in Chronic Kidney Disease Treatment: Still a Controversy? Nephron 135: 201-206.
Lin C.-N., I.-W. Wu, Y.-F.Huang, S.-Y. Peng, Y.-C. Huang, and H.-C. Ning. 2018. Measuring serum total and free indoxyl sulfate and p-cresyl sulfate in chronic kidney disease using UPLC-MS/MS. J. Food Drug Anal.
Al Za'abi, M., B. Ali, and M. Al Toubi. 2013. HPLC-fluorescence method for measurement of the uremic toxin indoxyl sulfate in plasma. J. Chromatogr. Sci. 51: 40-43.
Taki, K., S. Nakamura, M. Miglinas, A. Enomoto, and T. Niwa. 2006. Accumulation of indoxyl sulfate in OAT1/3-positive tubular cells in kidneys of patients with chronic renal failure. J. Ren. Nutr. Off. J. Counc. Ren. Nutr. Natl. Kidney Found. 16: 199-203.
Ito, S., M. Osaka, T. Edamatsu, Y. Koh, and M. Yoshida. 2016. Crucial Role of the Aryl Hydrocarbon Receptor (AhR) in Indoxyl Sulfate-Induced Vascular Inflammation. J. Atheroscler. Thromb. 23: 960-975.
Essono, S., Y. Frobert, J. Grassi, C. Créminon, and D. Boquet. 2003. A general method allowing the design of oligonucleotide primers to amplify the variable regions from immunoglobulin cDNA. J. Immunol. Methods 279: 251-266.
McCafferty, J., A. D. Griffiths, G. Winter, and D. J. Chiswell. 1990. Phage antibodies: filamentous phage displaying antibody variable domains. Nature 348: 552-554.
Dai, C., L. P. Kiss, and Y. Liu. 2008. Animal Models of Kidney Diseases. In Sourcebook of Models for Biomedical Research P. M. Conn, ed. Humana Press, Totowa, NJ. 657-664.

(Continued)

*Primary Examiner* — Phuong Huynh
(74) *Attorney, Agent, or Firm* — Fay Sharpe LLP

(57) ABSTRACT

The present invention relates to isolated monoclonal antibodies (mAbs) and/or antigen-binding fragments thereof that specifically recognize indoxyl sulfate, a protein-bound uremic toxin, isolated polynucleotide segment encoding the isolated antibodies and/or antigen-binding fragments thereof, and uses of such isolated anti-IS mAbs and/or antigen-binding fragments thereof to create immunoassay methods, device compositions, and pharmaceutical compositions applied in theragnosis of IS-related diseases.

9 Claims, 10 Drawing Sheets
(6 of 10 Drawing Sheet(s) Filed in Color)
Specification includes a Sequence Listing.

(56) References Cited

OTHER PUBLICATIONS

Yang, H.-C., Y. Zuo, and A. B. Fogo. 2010. Models of chronic kidney disease. Drug Discov. Today Dis. Models 7: 13-19.
Nangaku, M. 2004. Mechanisms of tubulointerstitial injury in the kidney: final common pathways to end-stage renal failure. Intern. Med. Tokyo Jpn. 43: 9-17.
Miwa, A., M. Yoshioka, A. Shirahata, and Z. Tamura. 1977. Preparation of specific antibodies to catecholamines and L-3,4-dihydroxyphenylalanine. I. Preparation of the conjugates. Chem. Pharm. Bull. (Tokyo) 25: 1904-1910.
Watanabe, H., T. Noguchi, Y. Miyamoto, D. Kadowaki, S. Kotani, M. Nakajima, S. Miyamura, Y. Ishima, M. Otagiri, and T. Maruyama. 2012. Interaction between two sulfate-conjugated uremic toxins, p-cresyl sulfate and indoxyl sulfate, during binding with human serum albumin. Drug Metab. Dispos. Biol. Fate Chem. 40: 1423-1428.

\* cited by examiner

COMPOSITIONS OF ISOLATED MONOCLONAL ANTIBODIES AND/OR ANTIGEN-BINDING FRAGMENTS THEREOF AGAINST INDOXYL SULFATE AND USES THEREOF

RELATED APPLICATIONS

This application claims benefit of priority from U.S. Provisional Application No. 62/659,256, filed on Apr. 18, 2018, the entirety of which is incorporated by reference herein.

A sequence listing is being submitted herein as an ASCII text file with the name "SP-4472-US-as-filed-SEQUENCE-LISTING.txt", created on Apr. 17, 2019, with a file size of 8,790 bytes.

BACKGROUND

Field of Invention

The present invention discloses an antigen-binding fragment specific for a uremic toxin, indoxyl sulfate (IS), and more specifically, the present invention relates to isolated monoclonal antibodies and/or antigen-binding fragments for specifically recognizing IS and uses of the same for theragnosis of IS-related disorders.

Description of Related Art

Uremia is characterized by pathological accumulation of a plurality of uremic toxins in the body, and such a debilitating condition will cause permanent loss of kidney function, gradually progress to stages of CKD and finally become life-threatening end-stage renal disease (ESRD). Uremic patients also have various clinical signs and symptoms involving nervous, digestive, circulatory, and skeletal systems (1). Although uremia and its resulting complications are generally controlled by dialysis treatments, including hemodialysis and peritoneal dialysis, in cases of patients advance to kidney failure, severe electrolyte disturbances may occur and wastes have accumulated to dangerous levels, and they consequently need kidney transplantation to stay live. Nonetheless, this treatment option is limited by the shortage of donor kidneys, the risk of death associated with surgery, and the subsequent life-long immunosuppression required to prevent organ rejection.

There are hundreds of potential uremic toxins have been identified. Three major categories are classified according to their physicochemical properties or their behaviors during dialysis: (a) the small, water-soluble, non-protein-bound compounds (molecular weight of <300 ID, for example, urea), (b) the larger middle molecules, mainly peptides, with a molecular weight of between 300 D and 12,000 D, and (c) the small protein-bound compounds (2). Binding to serum proteins like albumin limits the dialysis clearance of these protein-bound compounds. Consequently, the average levels of these toxins in patients undergoing hemodialysis may gradually accumulate up to 10 times and 20 times more than the normal levels.

IS and p-cresyl sulfate (PCS) are two prototypical albumin-bound toxins, and they both generated from dietary tryptophan and tyrosine fermented by microbiota in the gastrointestinal tract. Several groups demonstrate a pathological correlation between serum levels of IS and PCS on one hand and overall mortality and cardiovascular disease (CVD) on the other hand in CKD patients. Therefore, IS and PCS may not be only biomarkers to predict renal function and disease progression but also targets for therapeutically manipulating (3, 4).

AST-120 (Kremezin; Kureha Corporation, Tokyo, Japan) is an orally administered spherical carbon adsorbent that can adsorb various small molecule uremic toxins. It inhibits IS biosynthesis by adsorbing indole, the precursor of IS, in the intestines; thus indirectly reduces IS concentration in serum and urine (5). Although multiple prospective randomized clinical studies have been performed to demonstrate the potency of AST-120 to slow CKD progression, in conclusion, the benefit of adding AST-120 to standard therapy in patients with moderate to severe CKD was not supported by the data from these trials (6,7).

Analytical chemistry methods of IS detection and determination such as liquid chromatography-mass spectrometry (LC-MS) and high-performance liquid chromatography (HPLC) require a high-cost apparatus, complex sample preparation, large sample volume and thus are not suitable for measuring large numbers of biological samples (8). In contrast, enzyme-linked immunosorbent assays (ELISA) is simple to perform, and reagents are relatively inexpensive. By passing complicated sample pre-treatment allows automation of ELISA operation so that offers more accurate and reproducible results, faster turnaround times and fewer labor costs. Hoshi et al had developed a competitive ELISA method capable of quantitatively measuring IS, but the binding activity of the monoclonal antibody (mAb) 9A2F6, which is used in that method, would be inhibited by serum albumins of bovine or human (9,10). Sample deproteinization is in particular preferable or required prior to performing experimental steps, thus probably compromising laboratory or industrial applicability of that art.

Taken together, despite recent advances in the art, there continues to exist a substantial need for methods useful in improved qualitative or quantitative immunoassay, wherein an isolated anti-IS mAb is an essential functional component. Meanwhile, the performance of that immunoassay is insensitive to plasma proteins, especially albumin, ordinarily found in biological samples to be analyzed. There also continues to exist a substantial need for methods useful in efficient removal of IS from a subject by which treat IS-related disorders. These methods comprise administering to a subject an effective amount of isolated anti-IS mAbs, or coupling isolated anti-IS mAbs to a physical support hence allowing IS in a biological sample to be captured and removed by contacting each other.

SUMMARY

An aspect of the invention provides an isolated monoclonal antibody (mAb) and/or antigen-binding fragment thereof that specifically binds to IS, and it is alternatively referred as "anti-IS mAb".

Moreover, another aspect of the invention provides a multispecific binding molecule comprising a portion or a whole body of the isolated monoclonal antibody and/or antigen-binding fragment thereof as aforementioned.

Furthermore, another aspect of the invention provides an immunoassay for detecting indoxyl sulfate, thereby determining a concentration of indoxyl sulfate in a biological sample collected from in a subject.

Furthermore, another aspect of the invention provides a device composition for removing indoxyl sulfate.

Furthermore, another aspect of the invention provides a pharmaceutical composition for removing or reducing indoxyl sulfate in a subject.

Furthermore, another aspect of the invention provides an isolated polynucleotide segment encoding an isolated monoclonal antibody or antigen-binding fragment recognizing indoxyl sulfate as aforementioned.

Furthermore, another aspect of the invention provides an isolated monoclonal antibody and/or antigen-binding fragment thereof having an epitope and a Scatchard binding affinity on indoxyl sulfate excluding from L-tryptophan, indole and 3-indoleacetic acid.

In view of the foregoing aspects, the invention provides an isolated monoclonal antibody (mAb) and/or antigen-binding fragment thereof. The isolated monoclonal antibody (mAb) and/or antigen-binding fragment thereof comprise a heavy chain variable (VH) domain and a light chain variable (VL) domain. The VH domain comprises complementarity-determining regions (CDR)-H1, CDR-H2 and CDR-H3, and the VL domain comprises variable regions CDR-L1, CDR-L2 and CDR-L3. In an embodiment, amino acid sequences of CDRs comprises one or more of the sequences are set forth below: the CDR-H1 can be selected from any one of SEQ ID NOs: 1 or 11; the CDR-H2 can be selected from any one of SEQ ID NOs: 2 or 12; the CDR-H3 can be selected from any one of SEQ ID NOs: 3 or 13; the CDR-L1 can be selected from any one of SEQ ID NOs: 6 or 16; the CDR-L2 can be selected from any one of SEQ ID NOs: 7 or 17; and the CDR-L3 can be selected from any one of SEQ ID NOs: 8 or 18.

In an embodiment, the isolated monoclonal antibody and/or antigen-binding fragment thereof can be a full-length immunoglobulin molecule, a single-chain variable fragment (scFv), a variable fragment (Fv), a Fab fragment, a Fab' fragment, a single domain antibody (dAb), a multispecific binding molecule or any combination of an isolated human, chimeric, humanized, synthetic, recombinant antibody and/or an antigen-binding fragment thereof.

In an embodiment, the isolated monoclonal antibody and/or fragment thereof can be screened from an in-vitro surface display system.

In an embodiment, the isolated antibody and/or fragment thereof can be chemically modified or mixed with a pharmaceutically acceptable carrier.

In view of other aspects, the invention further provides a multispecific binding molecule, which comprises a portion or a whole body of the isolated monoclonal antibody and/or antigen-binding fragment thereof as aforementioned.

In an embodiment, the multispecific binding molecule specifically binds to indoxyl sulfate.

In view of other aspects, the invention further provides an immunoassay for detecting indoxyl sulfate, which comprises the isolated monoclonal antibody and/or antigen-binding fragment thereof as aforementioned, thereby determining a concentration of indoxyl sulfate in a biological sample collected from in a subject.

In an embodiment, the biological sample includes blood, serum, blood plasma, peritoneal fluids, urine and biopsy specimen.

In an embodiment, the biological sample contains albumin.

In view of other aspects, the invention further provides a device composition for removing indoxyl sulfate, which comprises the isolated monoclonal antibody and/or antigen-binding fragment thereof as aforementioned.

In an embodiment, the isolated monoclonal antibody and/or antigen-binding fragment thereof is conjugated to a solid phase.

In view of other aspects, the invention further provides a pharmaceutical composition for removing or reducing indoxyl sulfate in a subject, which comprises the isolated monoclonal antibody and/or antigen-binding fragment thereof as aforementioned.

In an embodiment, the pharmaceutical composition further comprises a medical adsorbent combined with the isolated monoclonal antibody and/or antigen-binding fragment thereof.

In an embodiment, the medical adsorbent includes an activated carbon absorbent.

In view of other aspects, the invention further provides an isolated polynucleotide segment, which encodes an isolated monoclonal antibody or antigen-binding fragment against indoxyl sulfate, and the isolated monoclonal antibody or antigen-binding fragment comprises one or more polypeptide sequences of a VH domain and a VL domain. In an embodiment, the VH domain can be listed as SEQ ID NOs:4 or 14, and the VL domain can be listed as SEQ ID NOs:9 or 19.

In view of other aspects, the invention further provides an isolated polynucleotide segment encoding an isolated monoclonal antibody or antigen-binding fragment recognizing indoxyl sulfate. In an embodiment, the isolated monoclonal antibody or antigen-binding fragment comprises one or more polypeptide sequences of CDR-H1 selected from any one of SEQ ID NOs: 1 or 11, CDR-H2 selected from any one of SEQ ID NOs: 2 or 12, CDR-H3 selected from any one of SEQ ID NOs: 3 or 13, CDR-L1 selected from any one of SEQ ID NOs: 6 or 16, CDR-L2 selected from any one of SEQ ID NOs: 7 or 17, and CDR-L3 selected from any one of SEQ ID NOs: 8 or 18.

In view of other aspects, the invention further provides an isolated monoclonal antibody and/or antigen-binding fragment thereof having an epitope and a Scatchard binding affinity on indoxyl sulfate excluding from L-tryptophan, indole and 3-indoleacetic acid.

With application to the aforementioned isolated monoclonal antibody and/or antigen-binding fragment thereof, in which the isolated monoclonal antibody and/or antigen-binding fragment thereof specifically recognizes IS, leading in excellent exhibition of sensitivity and dynamic breadth of detecting IS in the presence of albumin, thereby being applied to various uses, for example, immunoassays for detecting indoxyl sulfate, device compositions for removing indoxyl sulfate, pharmaceutical compositions for removing or reducing indoxyl sulfate in a subject, isolated polynucleotide segments encoding an isolated monoclonal antibody or antigen-binding fragment against indoxyl sulfate, and isolated monoclonal antibodies and/or antigen-binding fragments thereof having an epitope and a Scatchard binding affinity on indoxyl sulfate excluding from L-tryptophan, indole and 3-indoleacetic acid and the like.

BRIEF DESCRIPTION OF THE DRAWINGS

The patent or application file contains at least one drawing executed in color. Copies of this patent or patent application publication with color drawings will be provided by Office upon request and payment of the necessary fee. The disclosure can be more fully understood by reading the following detailed description of the embodiment, with reference made to the accompanying drawings as follows.

DETAILED DESCRIPTION

Figure 1A:
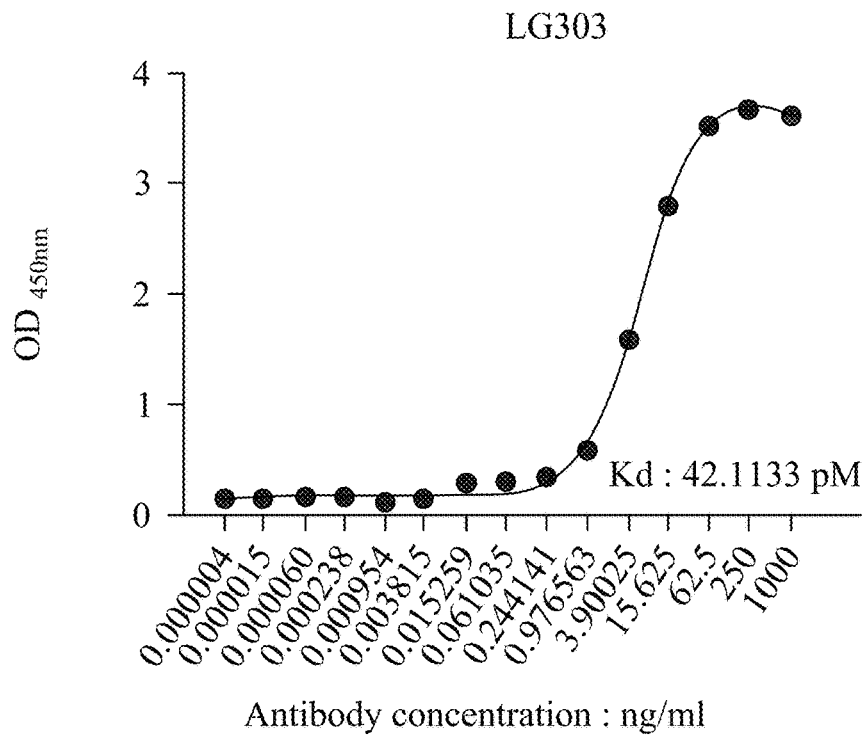
FIGS. 1A and 1B illustrates a titration curve of several isolated anti-IS monoclonal antibodies (mAbs) LG303 (FIG. 1A) and LG332 (FIG. 1B) to IS-BSA.

The embodiments of the invention will be apparent from the following detailed description, which proceeds with reference to the accompanying drawings, wherein the same references relate to the same elements.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

For purposes of interpreting this specification, the following definitions will apply and whenever appropriate, terms used in the singular will also include the plural and vice versa. Additional definitions are set forth throughout the detailed description.

The terms "a", "an", "the" and "said" as used herein are defined to mean "one or more" and include the plural unless the context is inappropriate.

The present invention discloses detecting and clearing methods in diagnosis and treatment of the uremia of comorbidities in patients with chronic kidney disease (CKD) by means of monoclonal antibodies (mAb) and/or fragments against indoxyl sulfate (IS), a protein-bound uremic toxin. With regard to diagnostic uses, an immunoassay for both qualitatively and quantitatively detecting IS in a biological sample is provided. To efficiently remove circulating IS in a subject, two strategies are adopted that one is to administer anti-IS mAbs at an effective dose to that subject, and the other is to absorb IS by pass a biological sample through a solid phase support conjugated with anti-IS mAbs. The said biological sample may be blood, serum, plasma, peritoneal fluids, urine, biopsy specimen etc. Since those biological samples collected from subjects often contain a variety of plasma proteins, the performance of binding activities of the aforementioned anti-IS mAbs should not be interfered by any plasma protein, especially the most abundant albumin. In spite of IS has been regarded to exacerbate CKD and some other nephropathies, but the utility of this invention does not be restricted to nephrology.

The term "subject" includes human and non-human animals.

Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs can include but not be limited to phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions can be achieved by generating sequences in which the third position of one or more selected (or all) codons is substituted with mixed-base and/or deoxyinosine residues.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "antibody" refers to an intact immunoglobulin molecule or a functional fragment thereof. Naturally occurring antibodies typically comprise a tetramer which is usually composed of at least two heavy (H) chains and at least two light (L) chains. Each heavy chain is comprised of a heavy chain variable region (abbreviated herein as VH) and a heavy chain constant region, usually comprised of three domains (CH1, CH2 ad CH3). Heavy chains can be of any isotype, including IgG (IgG1, IgG2, IgG3 and IgG4 subtypes), IgA (IgA1 and IgA2 subtypes), IgM and IgE. Each light chain is comprised of a light chain variable region (abbreviated herein as VL) and a light chain constant region (CL). Light chain includes kappa chains and lambda chains. The combination of VH and VL domains is typically responsible for antigen recognition, while the CH domain may mediate the binding of the immunoglobulin to host tissues or factors, including various cells of the immune system (e.g., effector cells) and the first component (C1q) of the classical complement system. The VH and VL domains can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen.

The term "antibody fragment" or "a specific binding fragment thereof" can refer to a whole structure or a portion of an intact antibody that includes Fab fragments, Fab' fragments, F(ab')2 fragments, Fd fragments, Fv fragments and disulfide linked Fv fragments; single-chain antibody molecules (scFv); (scFv)$_2$ or called diabodies, (scFv)$_3$ or called triabodies, (scFv)$_4$ or called tetrabodies, single domain antibodies (dAb), single domain antibodies (dAb), minibodies, nanobodies, and multispecific antibodies formed from antibody fragments. Moreover, the antibody and/or antigen-binding fragment thereof can also refer to monoclonal antibodies, polyclonal antibodies, multispecific antibodies (e.g., bispecific antibodies) formed from at least two intact antigen-binding fragments, human antibodies, humanized antibodies, camelised antibodies, chimeric antibodies or murine antibodies.

The term "antibody drug conjugate (ADC)" or "immunoconjugate" as used herein refers to the linkage of an antibody or an antigen binding fragment thereof with another agent, such as a chemotherapeutic agent, a toxin, an immunotherapeutic agent, an imaging probe, and the like. The linkage can be covalent bonds, or non-covalent interactions such as through electrostatic forces. Various linkers, known in the art, can be employed in order to form the antibody drag conjugate. Additionally, the antibody drag conjugate can be provided in the form, of a fusion protein that may be expressed from, a polynucleotide encoding the immunoconjugate. As used herein, "fusion protein" refers to proteins created through the joining of two or more genes or gene fragments which originally coded for separate proteins (including peptides and polypeptides). Translation of the fusion gene results in a single protein with functional properties derived from each of the original proteins.

The term "isolated" means that the immunoglobulin, antibody or polynucleotide, as the case may be, exists in a physical milieu distinct from that in which it may occur in nature.

The "epitope" or "antigenic determinant sites" is a portion of an antigen molecule that is responsible for specific interactions with the antigen-binding domain of an antibody. An antigen-binding domain may be provided by one or more antibody variable domains. A functional antigen-binding fragment may be brought off by rounds of recombining and screening work from isolated VH and VL domains of mAbs.

The term "complementarity determining regions" ("CDR") are defined parts of the variable chains in antibodies, where these molecules bind to their specific antigen. In this disclosure, the CDR regions in the heavy chain are typically referred to as CDR-H1, CDR-H2 and CDR-H3 and in the light chain as CDR-L1, CDR-L2 and CDR-L3. They are numbered sequentially in the direction from the amino terminus to the carboxy terminus.

The terms "monoclonal antibody" or "monoclonal antibody composition" as used herein refer to a preparation of antibody molecules of single molecular composition. A monoclonal antibody composition displays a single binding specificity and affinity for a particular epitope.

The isolated monoclonal antibody and/or antigen-binding fragment thereof refers to a protein or peptide produced from cDNA-, recombinant RNA-, or any other synthetic-origin, or some combination thereof; as well as to proteins and peptides that, by virtue of their origin or source of derivation, either (1) are not associated with proteins found in nature, (2) are free of other proteins from the same source, e.g. free of murine proteins, (3) are expressed by a cell from a different species, or (4) do not occur in nature.

The "anti-IS mAb" herein indicates a generic term of antibody formats and/or fragments specifically binding to IS.

Moreover, the invention also provides methods to generate isolated anti-IS mAbs and/or fragments thereof. Furthermore, the aforementioned isolated anti-IS mAb are exemplified by two isolated mAbs, the LG303 and LG332, named after two hybridoma cell lines which respectively secrete them.

Furthermore, the invention also provides polynucleotide sequences encoding variable domains of the aforementioned anti-IS mAb, which consist of a heavy chain variable (VH) domain and a light chain variable (VL) domain. For example, the SEQ ID NOs: 5 and 15 of antibody VH domain and the SEQ ID NOs: 10 and 20 of antibody VL domain respectively correspond to LG303 and LG332.

The invention also provides amino acid sequences translated from the aforementioned polynucleotide sequences. For example, the SEQ ID NOs: 4 and 14 of antibody VH domain and the SEQ ID NOs: 9 and 19 of antibody VL domain respectively correspond to LG303 and LG332. The complementarity-determining region (CDR)-H1, CDR-H2 and CDR-H3 within the VH domain and CDR-L1, CDR-L2 and CDR-L3 within the VL domain of the aforementioned antibodies are also identified.

In a specific embodiment, amino acid sequences of the aforementioned CDRs corresponding to LG303 and LG332 are set forth below: the SEQ ID NOs: 1 and 11 of CDR-H1; the SEQ ID NOs: 2 and 12 of CDR-H2; SEQ ID NOs: 3 and 13 of CDR-H3; the SEQ ID NOs: 6 and 16 of CDR-L1; the SEQ ID NOs: 7 and 17 of CDR-L2; the SEQ ID NOs: 8 and 18 of CDR-L3.

The terms "percent (%) sequence identity" or "homology" are defined as the percentage of amino acid residues or nucleotides in a candidate sequence that are identical with the amino acid residues or nucleotides in the reference sequences after aligning the sequences and introducing gaps, if necessary, to achieve the maximum percent sequence identity, and excluding conservative nucleic acid substitutions. Optimal alignment of the sequences for comparison may be produced, besides manually, by means of local homology algorithms known in the art or by means of computer programs which use these algorithms (e.g., BLAST P).

Moreover, the nucleotide sequences and the amino acid sequences mentioned below are listed in Sequence listing.

Furthermore, the invention also provides methods to use the aforementioned isolated anti-IS mAb as diagnostic reagents for IS-related disorders.

Furthermore, the invention also provides methods to use the aforementioned isolated anti-IS mAb as therapeutic reagents for IS-related disorders.

Furthermore, the invention also provides methods to use the aforementioned isolated anti-IS mAb as IS-displacing reagents for cleaning extracorporeal biological fluids.

Furthermore, the invention also provides methods to use the aforementioned isolated anti-IS mAb in an immunoassay, a device composition or a pharmaceutical composition.

Furthermore, the invention also provides methods to develop the foregoing immunoassay, device composition and pharmaceutical composition.

Furthermore, the invention also provides an immunoassay comprising the aforementioned isolated anti-IS mAb, for qualitative and quantitative detection of IS in a biological sample.

Furthermore, the invention also provides a method to diagnose IS-related disorders by utilizing the foregoing immunoassay.

Furthermore, the invention also provides a device composition comprising the aforementioned isolated anti-IS mAb, for extracorporeal removing IS or reducing uremia burden of from biological fluids of a subject.

Furthermore, the invention also provides a method to remove IS or reduce uremia burden by administrating a pharmaceutical composition comprising an effective amount of the aforementioned isolated anti-IS mAb.

In one embodiment, the aforementioned isolated anti-IS mAbs can be conjugated to a solid phase for physical support when they are used in an immunoassay or a device composition.

In one embodiment, the foregoing pharmaceutical composition foregoing can be used in a subject in need of mitigating risks of renal failure or CVD with concomitant CKD.

In one embodiment, the foregoing pharmaceutical composition can be used in a combination with other medicaments, i.e. orally administered spherical carbon adsorbents, angiotensin-converting enzyme inhibitors (ACEI), angiotensin receptor blockers (ARB) and active vitamin D.

The term "device composition" used herein refers to a composition for being implemented in a specific device. In one embodiment, the foregoing device composition may be incorporated with a hemodialysis or plasmapheresis system for a subject in need of mitigating risks of renal failure or CVD with concomitant CKD.

In one embodiment, the foregoing device composition may be incorporated with an apparatus for cleaning extracorporeal blood which the blood is fractioned into a first cleaned fraction and a second cleaned fraction. The second cleaned fraction is produced by removing toxins bound on proteins and/or toxins dissolved in the plasma.

In one embodiment, the biological sample (or fluid) to be assayed includes blood, serum, blood plasma, peritoneal fluids, urine and biopsy specimen.

In one embodiment, the biological sample to be assayed contains plasma proteins, i.e. albumin.

Certain exemplary embodiments according to the present disclosure are described as below, but these embodiments should not be considered as limiting the present invention. Various modification and changes can be made by one of ordinary skills in the art to which the present invention pertains, without departing from the spirit and scope of the present invention.

Compositions for Specifically Binding IS

According to one embodiment of this disclosure, an IS binding molecule is provided. In this embodiment, the binding molecule can be an isolated mAb and/or antigen-binding fragment thereof (hereinafter referred as "anti-IS mAb") which can specifically recognize/bind IS. The anti-IS mAb comprises a heavy chain variable (VH) domain comprising complementarity-determining regions (CDR)-H1, CDR-H2 and CDR-H3, and a light chain variable (VL) domain comprising variable regions CDR-L1, CDR-L2 and CDR-L3. Amino acid sequences of CDRs comprises one or more of the sequences are set forth below: CDR-H1 selected from any one of SEQ ID NOs: 1 or 11; CDR-H2 selected from any one of SEQ ID NOs: 2 or 12; CDR-H3 selected from any one of SEQ ID NOs: 3 or 13; CDR-L1 selected from any one of SEQ ID NOs: 6 or 16; CDR-L2 selected from any one of SEQ ID NOs: 7 or 17; and CDR-L3 selected from any one of SEQ ID NOs: 8 or 18.

In some embodiment, the amino acid sequence of the VH domain of the anti-IS mAb can be SEQ ID NOs: 4 or 14, or any sequence that exhibits, at least, 80%, 90%, 95%, or 99% (or any percentage in between) identity with SEQ ID NOs: 4 or 14. Also, the amino acid sequence of the VL domain of the anti-IS mAb can be SEQ ID NOs: 9 or 19, or any sequence that exhibits, at least, 80%, 90%, 95% or 99% (or any percentage in between) identity with SEQ ID NOs: 9 or 19.

Immunoassays Used for Detection and Quantitation of IS and Clinical Diagnosis

The term "immunoassay" refers to a method of detecting an analyte in a sample involving contacting the sample with an antibody that specifically binds to the analyte and detecting binding between the antibody and the analyte. The immunoassay said herein can be applied to various types of immunological or biochemical diagnosis techniques utilizing the antigen-antibody reaction caused by the mAb. Such assay methods include, but are not limited to, radioimmunoassay, immunohistochemistry assay, in situ hybridization assay, competitive-binding assay, Western Blot analyses and ELISA assay. Moreover, such assay techniques include (a) use of a fluorescent antibody or a chemical staining method in which the mAb is labeled with dye, such as a fluorescent dye, to allow the presence of the linkage between the mAb and the antigen to be visibly observed, (b) an enzyme-antibody method using an enzyme instead of the fluorescent dye to label the mAb, (c) an ELISA method using a protein-labeled secondary antibody to measure an amount of antigen or the like, (d) a radioimmunoassay method in which the mAb is labeled with isotope, and (e) an immunoprecipitation method utilizing an agglutination reaction caused by the antigen-antibody reaction.

The present invention relates to an immunoassay, either quantitative or qualitative for detecting IS levels in a biological sample, including determination of normal and abnormal levels. In some embodiments, the biological sample can be blood, serum, plasma, peritoneal fluids, urine, biopsy specimens etc. Moreover, the biological sample can be analyzed in the presence of plasma proteins, i.e. albumin. In a further embodiment, the immunoassay provided in this invention comprises the aforementioned isolated anti-IS mAb and that can be used to diagnose a disorder or diseases, which is estimated by the concentration of a biological sample collected from a subject. One example of said pathophysiological condition or a clinical sign can be uremia or CKD.

Device Composition for Removing IS

According to one embodiment of this disclosure, a device composition for IS removal or reduction is provided. In some embodiments, the aforementioned isolated anti-IS mAbs are conjugated to a solid phase for physical support such as resin beads of agarose, glass, plastic or magnetic, a dialysis membrane, and a hollow fiber tube. Moreover, the dialysis membrane or hollow fiber tube which is conjugated with isolated anti-IS mAb can be incorporated with a hemodialysis or plasmapheresis system.

A method for removal of uremic toxins bound to albumin in blood of a patient is described in U.S. Pat. No. 8,206,591 B2. This method includes introducing a displacer substance into the blood such that the displacer substance displaces uremic toxins bound to the albumin. The unbound uremic toxins are then removed by extracorporeal renal displacement treatment before the blood is returned to the patient. The displacer substance is for example the aforementioned isolated anti-IS mAb. This method is suggested to be used in a combination with other medicaments, i.e. orally administered spherical carbon adsorbents, angiotensin-converting enzyme inhibitors (ACEI), angiotensin receptor blockers (ARB) and active vitamin D.

In a more specific embodiment, anti-IS mAbs were coupled to agarose beads by preforming reductive amination reaction, and the mAb-conjugated beads were packed into an empty column, for forming IS-removal column. Biological fluids were passes through that IS-removal column twice by a peristaltic pump. Untreated and treated plasma samples were analyzed quantitative mass spectrometry (liquid chromatography-tandem mass spectrometry, LC-MS/MS) to evaluate IS removal rates. Percentages (%) of the IS removal rate were calculated by ([IS, untreated]−[IS, treated])/[IS, untreated]×100%.

Pharmaceutical Composition for Removing or Reducing IS in a Subject

According to one embodiment of this disclosure, a pharmaceutical composition for removing or reducing IS in a subject is provided. Amounts and regimens for the administration of anti-IS mAbs may be determined readily by those with ordinary skill in the clinical art of treating IS-related disorders. A desired dose can be administered in one or more applications to obtain the desired results. Pharmaceutical compositions according to the present embodiments may be provided in unit dosage forms. The pharmaceutical compositions may be administered in any appropriate pharmacological carrier for administration. They can be administered in any form that effect prophylactic, palliative, preventive or curing conditions of uremia conditions in human or animal patients. For use in accordance with the present embodiments, isolated anti-IS mAbs may be provided as a pharmaceutical composition comprising a pharmaceutically acceptable carrier or diluent and, as active ingredient, an isolated mAbs and/or fragment thereof against IS. The composition contains the anti-IS mAb in an amount sufficient to antagonize (fully or partially) the cytotoxicity of IS or native binding to the cell biological receptors of uremic toxins, for example, anion transporters (OATs) (10) or aryl hydrocarbon receptor (AhRs)(11) in patients in need of such antagonizing. The pharmaceutical composition can comprise at least one of isolated anti-IS mAbs described above. Moreover, that pharmaceutical composition can be used in combination with in a combination with other medicaments, i.e. orally administered spherical carbon adsorbents, angiotensin-converting enzyme inhibitors (ACEI), angiotensin receptor blockers (ARB) and active vitamin D. In some practices, the said medicament can be an activated carbon absorbent, e.g. AST-120.

Polynucleotide and Polypeptide Sequences of Variable Regions of Isolated Anti-IS mAb According to one embodiment of this disclosure, polynucleotide sequences or segments encoding the aforementioned isolated anti-IS mAb and/or antigen-binding fragment thereof are also provided. In some embodiments, the polynucleotide sequence which encodes the VH domain of SEQ ID NO: 4 means the DNA sequence set forth as SEQ ID NO: 5 or any polynucleotide sequence sharing at least 80%, 90%, 95%, or 99% (or any percentage in between) identity with SEQ ID NO: 5. Meanwhile, the polynucleotide sequence which encodes the VL domain of SEQ ID NO: 9 means the DNA sequence set forth as SEQ ID NO: 10 or any polynucleotide sequence sharing at least 80%, 90%, 95%, or 99% (or any percentage in between) identity with SEQ ID NO: 10.

Alternatively, of the isolated nucleic acid of this embodiment, the polynucleotide sequence which encodes the VH domain of SEQ ID NO: 14 comprises a sequence set forth as SEQ ID NO: 15 or any nucleotide sequence which exhibits, at least, 80%, 90%, 95%, or 99% (or any percentage in between) identity with SEQ ID NO: 15. Meanwhile, the nucleic fragment which encodes the VL domain of SEQ ID NO: 19 comprises a sequence set forth as SEQ ID NO: 20 or any nucleotide sequence which exhibits, at least, 80%, 90%, 95%, or 99% (or any percentage in between) identity with SEQ ID NO: 20.

In this embodiment, the polynucleotide sequences include substantially identical to those coding for the amino acid sequences as described above. Substantially identical sequences may also comprise mutagenized sequences, including sequences comprising silent mutations. A mutation may comprise one or more nucleotide residue changes, a deletion of one or more nucleotide residues, or an insertion of one or more additional nucleotide residues. Substantially identical sequences may also comprise various nucleotide sequences that encode for the same amino acid at any given amino acid position in an amino acid sequence disclosed herein, due to the degeneracy of the nucleic acid codons. The polynucleotide sequences encoding anti-IS mAbs and/or antigen-binding fragment thereof can be obtained by any known method in the art. For example, if the nucleotide sequence of an antibody is known, a polynucleotide encoding the antibody may be assembled from chemically synthesized oligonucleotides. This would involve, for example, the synthesis of overlapping oligonucleotides containing portions of the sequence encoding the antibody, annealing and ligating those oligonucleotides, and then amplifying the ligated oligonucleotides by PCR (12).

In general, the polynucleotide sequences which encode anti-IS mAbs and/or antigen-binding fragment thereof can be recombined into an expression vector where they may be a segment of an open reading frame. In some practices, the expression vector is introduced into a subject or host cells to generate proteinous products that specifically recognize IS as provided by the aforementioned embodiments. More detailed, the polynucleotide segments of this embodiment are recombinant DNA or RNA and, in some cases, they may be segregated by non-coding regulatory elements or introns. Preferably, the isolated nucleic acids are of cDNA molecule. To create a scFv gene, the VH- and VL-encoding DNA fragments are operatively linked to another fragment encoding a flexible linker, e.g., encoding the amino acid sequence (Gly4-Ser)3 (SEQ ID NO: 21), such that the VH and VL sequences can be expressed as a contiguous single-chain protein, with the VL and VH regions joined by the flexible linker. For antibodies obtained from using phage display techniques, the isolated nucleic acids encoding the anti-IS antibodies provided by the aforementioned embodiments can be recovered from various phage clones of the library (13). The disclosed polynucleotides can also be generated from any other suitable source of nucleic acids, such as an antibody cDNA library, or a cDNA library isolated from any tissue or cells expressing the antibody (e.g., from hybridoma cells selected to express an antibody).

In some embodiments, any of the disclosed polynucleotide sequences may be incorporated into an expression vector, thereby being expressed under control of a desired promoter. Suitable vectors for expression in various human and animal cell types are known in the art. Suitable host cells may include but not be limited to HEK293, CHO, Pichia, SF9, E. coli BL21 and/or other human or non-human cell lines. In some embodiments, whenever the cultured cells express the recited nucleic acids on an expression vector, whether transiently or stably, the method to generate anti-IS mAb and/or antigen-binding fragment thereof is disclosed herein.

5/6 Nephrectomy (5/6 Nx) Rat Chronic Kidney Disease (CKD) Model and Treatment

Unilateral ureteral obstruction (UUO), Adriamycin (ADR) nephropathy as well as 5/6 Nx are classical animal models of CKD. The UUO model is quickly and completely obstructed tubules and shows characteristics between different pathological stages and fibrosis, including infiltration of inflammatory cells, apoptosis of tubular cells, activation of myofibroblasts (fibroblasts), fibronectin and type I collagen deposition. ADR nephropathy is commonly used simulation models currently human glomerular disease, which is characterized by a large number of proteinuria, renal tubular casts, renal tubular collapse, focal segmental glomerulosclerosis (FSGS, also called as progressive focal segmental sclerosis) and glomerular sclerosis, severe renal interstitial and the formation of inflammation. The 5/6 Nx model is featured by arterial hypertension, proteinuria, and glomerular sclerosis. Among these available experimental models, the 5/6 Nx of rats is most used for studies of progressive renal disease. This is because the features of this experimental procedure are common to CKD observed in humans. The 5/6 Nx has also been established to test new therapies and has been proven to be clinically relevant (14,15).

Tubulointerstitial fibrosis often pathologically associated with CKD presents a number of common characteristics including: a persistent inflammatory cell infiltrate; an increase in interstitial cell number with the appearance of myofibroblasts expressing the cytoskeletal protein a-smooth muscle actin (a-SMA); tubular atrophy and epithelial apoptosis; utter destruction of the peritubular capillaries; and, accumulation of extracellular matrix (ECM) (16). In normal kidneys, the production of different collagen molecules is compartmentalized, with tubular epithelial cells (TECs) as the principal cells of collagen type IV production, and resident fibroblasts producing collagens type I and III. In tubulointerstitial fibrosis, expansion of the ECM is marked by accumulation of interstitial collagens and resident fibroblasts transdifferentiate into a-SMA-positive myofibroblasts. In addition, expression of collagen type IV, normally locating in glomerular and tubular basement membranes, is no longer restricted and it may be also observed in the interstitium. Regional differences of caspase-cleaved cytokeratin 18 (M30) might be regarded as a pharmacodynamic biomarker of treatment regimens because it is released from proximal tubular cells and podocytes undergo apoptosis induced by renal injury in 5/6 Nx rats. Hence, effects of anti-IS mAbs for intervening IS-related tissue atrophy should be elucidated by histological staining and specialized IHC examination on collagens type I and IV for excessive ECM deposition, a-SMA for assessing glomerulosclerosis and M30 for apoptosis index of glomerular cells.

To illustrate the properties as well as embodied practices of isolated anti-IS mAbs and/or antigen-binding fragments thereof described above, there are several examples shown below.

EXAMPLES

Example 1: Preparation of Antigenic IS Conjugates

To prepare a complete antigen from IS of a hapten, its potassium salts (Santa Cruz Biotechnology) were chemically coupled with a panel of carrier materials: the Imject™ Blue Carrier™ Protein (BCP, Thermo Scientific), bovine serum albumin (BSA, Thermo Scientific) and agarose gel beads crosslinked by DADPA (diaminodipropylamine) (CarboxyLink™ Coupling Gel, Thermo Scientific). In brief, 10 mg of IS in 1 mL PBS was mixed with three carrier materials at the equal preparation (10 mg/mL in PBS) in a tube, respectively. The 2-mL mixture was added with 0.25 mL 37% formaldehyde or 50% glutaraldehyde and incubated at 50° C. for 72 hours (the Mannich-type reaction (17). After the coupling reaction, IS-carrier protein conjugates were purified by chromatography with a column of Sephadex G-25 resin (GE Healthcare) and their concentrations were determined by the Bradford reagent (Bio-Rad). As for the IS-DADPA agarose conjugates, coupled gel beads were washed three times with deionized water and reconstitute in 5 mL PBS.

Example 2: Generation of Anti-IS mAbs by the Hybridoma Technique

Mice (8-10-week-old female BALB/c) were immunized with antigenic IS conjugates prepared as above and two immunization routes were adopted. One is conventional intraperitoneal (IP) immunization. In this route, IS-BCP/IS-BSA conjugates (50 µg in 100 µL PBS) or IS-DADPA agarose conjugates (100 µL) were mixed with equal volume of Complete Freund's Adjuvant (CFA, Sigma-Aldrich) or Incomplete Freund's Adjuvant (IFA, Sigma-Aldrich). Each mouse was received four immunizations in four weeks, including the first priming and three boosters. In the other route of direct spleen immunization. 5 µg of IS-BCP conjugates in 5 µL PBS was first injected to spleens of five mice with 34G needle. If antigenic responses were successfully primed, these mice were subsequently boosted with IS-BCP conjugates (50 µg in 200 µL IFA) for three times through subcutaneous (SC) injection. Before fusion with myeloma cells, IS-binding splenocytes were enriched by attaching them onto IS conjugates-coated 10-cm culture plates (Nunc™, Thermo Scientific) and non-binders were washed off with culture media flushing. In both routes, serum titers of mice were monitored by ELISA or flow cytometry before each immunization action, and when intended titers were reached, mice were sacrificed for hybridoma screening. The screening criteria were that distributed cells whose supernatants can recognize free form IS were picked to build single clones (limiting dilution), and those who only recognize IS conjugates but not unreactive to free form IS, or reactive to unconjugated carriers should be discarded. The isolated hybridoma cell line was injected into the abdomen of a BALB/c mouse, and the resultant ascitic fluid was collected. The collected ascitic fluid was purified by an affinity chromatography protein A column (GE Healthcare) so as to extract the desired antibody. The maximum concentration of the purified antibody was 10 mg/mL.

Example 3: Competitive ELISA to Test mAb Specificity

In competitive ELISA described here, anti-IS mAbs or IS conjugates are interchangeably to assume the free analyte or immobilized catcher. Which role these two reactants being appointed depends on experimental design.

In the case of using anti-IS mAbs as the free analyte (IS conjugates are coated on microtiter plates), a secondary antibody like HRP-conjugated goat IgG against mouse IgG.Fcγ fragment might be employed as reporter. Concentrations of IS conjugates for plate coating range from 50 ng/mL to 50 µg/mL. Anti-IS mAbs can be used at a range between 10 µg/mL and 10 µg/mL.

When anti-IS mAbs are immobilized as catchers, the IS analyte should be conjugated with an enzyme reporter for plotting a standard curve, i.e. HRP in this case. Coating can be effectively performed at a concentration between 1 ng/mL to 50 µg/mL. IS-HRP conjugate can be prepared by the Mannich-type addition shown in the previous section, and working concentrations range from 10 ng/mL to 10 µg/mL. Reference IS standards can be used from 1 µg/mL to 500 µg/mL to plot standard curve.

To preliminarily test the specificity of mAb candidates, their activities against IS, indole, L-tryptophan, and 3-indoleacetic acid (all chemical compounds are from Sigma-Aldrich) were compared in a competitive ELISA. Wells of ELISA plates (Corning Costar) were coated with the IS-BSA conjugate (0.5 µg/mL, 100 µL per well) at 4° C. overnight and were blocked with 300 µL of PBST (PBS with 0.05% TWEEN® 20) containing 3% BSA at 37° C. for one hour followed by three times of PBST washing. Two-fold serial dilutions of crudely purified mAb candidates (16-128 ng/mL) spiked with compounds at 20 µg/mL and a blank control in the mentioned blocking buffer were added to antigen-coated wells. After 30 to 60 minutes of incubation at room temperature, wells were aspirated and washed with 300 µL of PBST for three times. Then, secondary antibodies used at 1:5000 in PBST, 100 µL of HRP-conjugated goat IgG anti-mouse IgG (Leadgene Biomedical) were poured into each well for another 30-minute incubation at room temperature. Before adding the TMB (3,3',5,5'-tetramethylbenzidine) substrate solution (KPL) for color development, wells were washed six times with PBST. When colors were developed to comparable levels, the reaction was stopped by adding 0.1 N sulfuric acid and activities of mAb candidates were analyzed by a microtiter plate reader (Molecular Devices) measuring optical absorbance at 450 nm. Percentages of relative binding activities of tested candidates were calculated as $B/B_0 \times 100\%$ [(mean absorbance of compounds-spiked wells)/(mean absorbance of blank control wells)] were calculated. Tested candidate would not be selected if its binding activity to IS were significantly competed by competitors among indole, L-tryptophan, and 3-indoleacetic acid (criteria: $Bis/B_0 < 30\%$; $Bcompetitors/B_0 > 70\%$).

Example 4: Characterization of Two Clones of mAbs Against IS

Figure 1B:
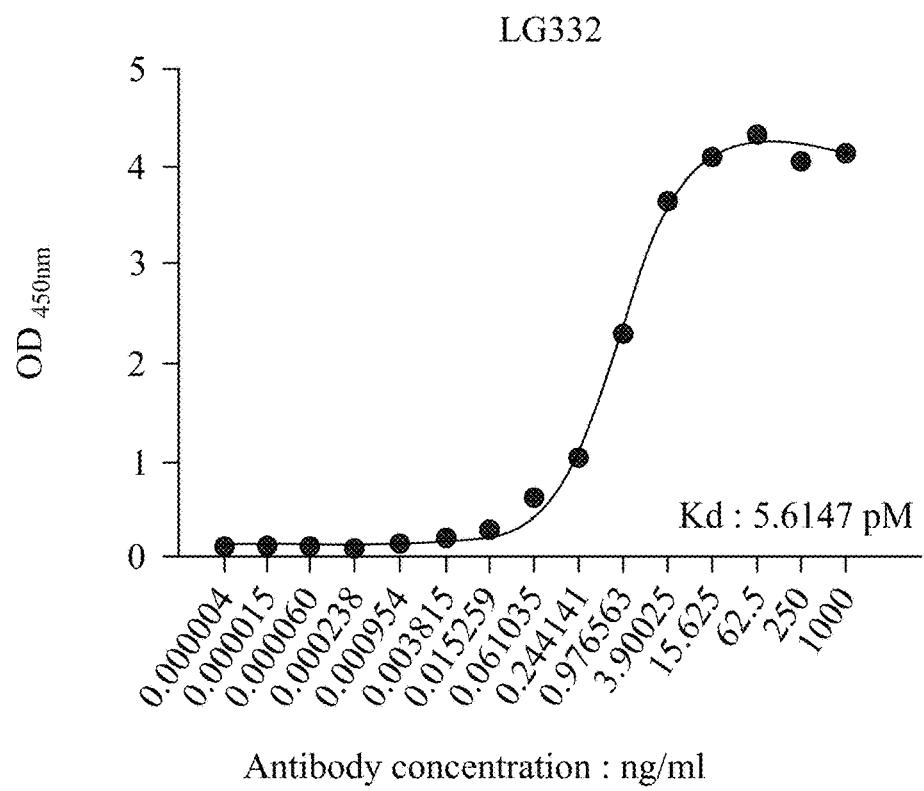

Through two consecutive rounds of screening, two mAbs, LG303 and LG332, were selected from dozens of candidates since their outstanding affinity and specificity to IS. The titration curve and estimated Kd (the equilibrium dissociation constant) of LG303 and LG332 were shown in FIG. 1A and FIG. 1B, and both mAbs behave a Scatchard binding affinity on IS.

Their isotypes were identified by a mouse mAb isotyping kit (Thermo Fisher) that respectively attributed LG303 to IgG1/k and LG332 to IgG2a/k. With coupled reverse transcription-PCR and the Mouse Ig Primer Set (Merck Millipore), gene sequences of antibody variable regions were resolved from mRNA extracts of hybridoma cells. The polynucleotide sequence of the LG303 VH domain (SEQ ID NO:5) was translated into the polypeptide sequence as the SEQ ID NO: 4, and three CDR sequences of which were the SEQ ID NO: 1 (CDR-H1), SEQ ID NO: 2 (CDR-H2), and SEQ ID NO: 3 (CDR-H3). The polynucleotide sequence of the LG303 VL domain (SEQ ID NO: 10) was translated into the polypeptide sequence as the SEQ ID NO: 9, and three CDR sequences of which were the SEQ ID NO: 6 (CDR-L1), SEQ ID NO: 7 (CDR-L2), and SEQ ID NO: 8 (CDR-L3). The polynucleotide sequence of the LG332 VH domain (SEC ID NO:15) was translated into the polypeptide sequence as the SEQ ID NO: 14, with three CDR regions with sequences of SEQ ID NO: 11 (CDR-H1), SEQ ID NO: 12 (CDR-H2), and SEQ ID NO: 13 (CDR-H3). The polynucleotide sequence of the LG332 VL domain (SEQ ID NO: 20) VL domain was translated into the polypeptide sequence as the SEQ ID NO: 19, with three CDR regions with sequences of SEQ ID NO: 16 (CDR-L1), SEQ ID NO: 17 (CDR-L2), and SEQ ID NO: 18 (CDR-L3).

Figure 2A:
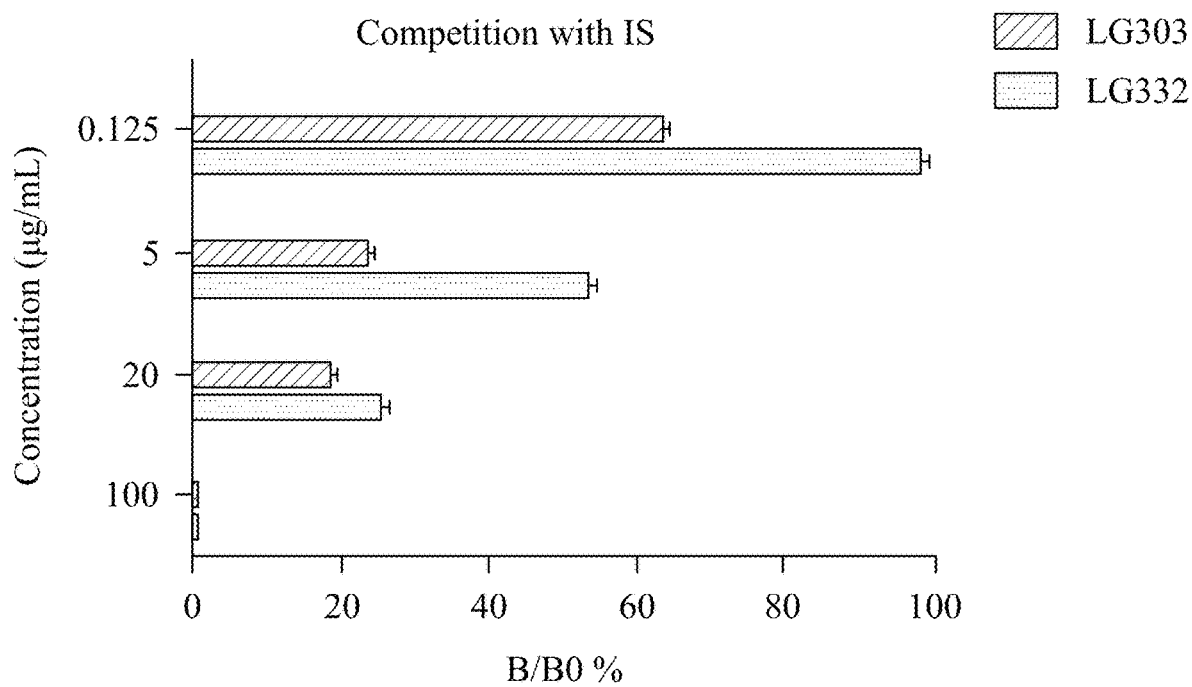
FIGS. 2A to 2D illustrate bar diagrams showing B/B % of several isolated anti-IS mAbs LG303 and LG332 to IS-BSA in the presence of different concentrations of IS (FIG. 2A), L-tryptophan (FIG. 2B), indole (FIG. 2C) and 3-indoleacetic acid (FIG. 2D) respectively.
Figure 2B:
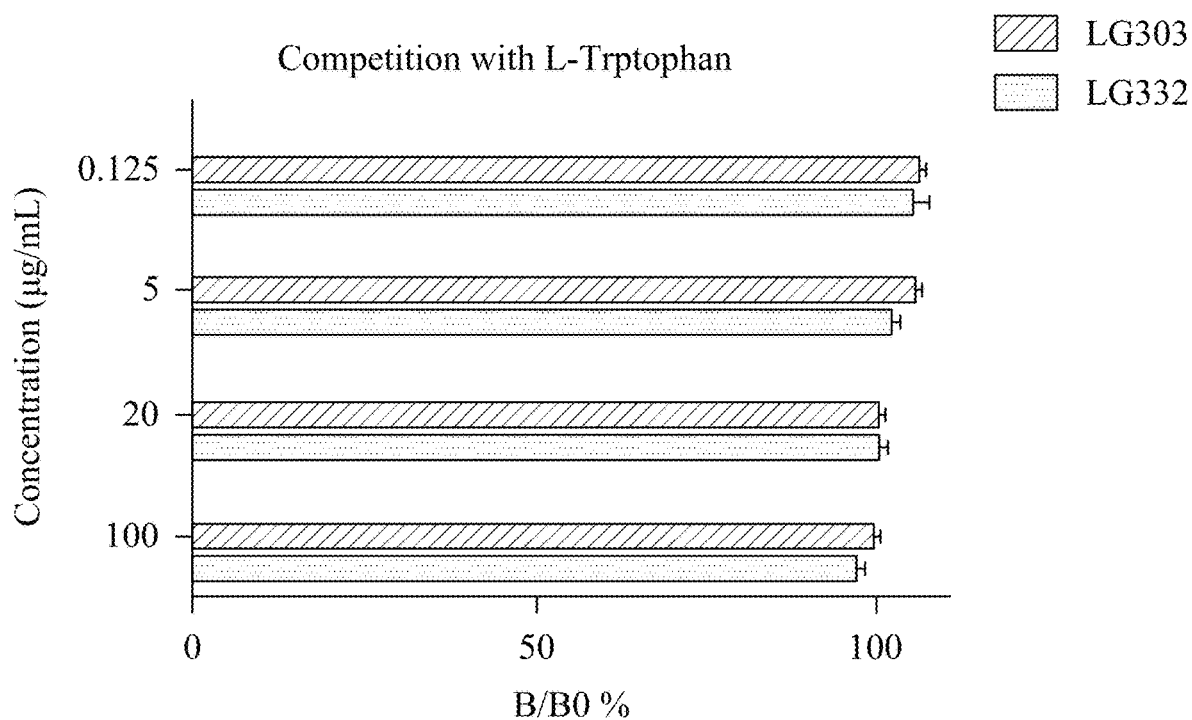
Figure 2C:
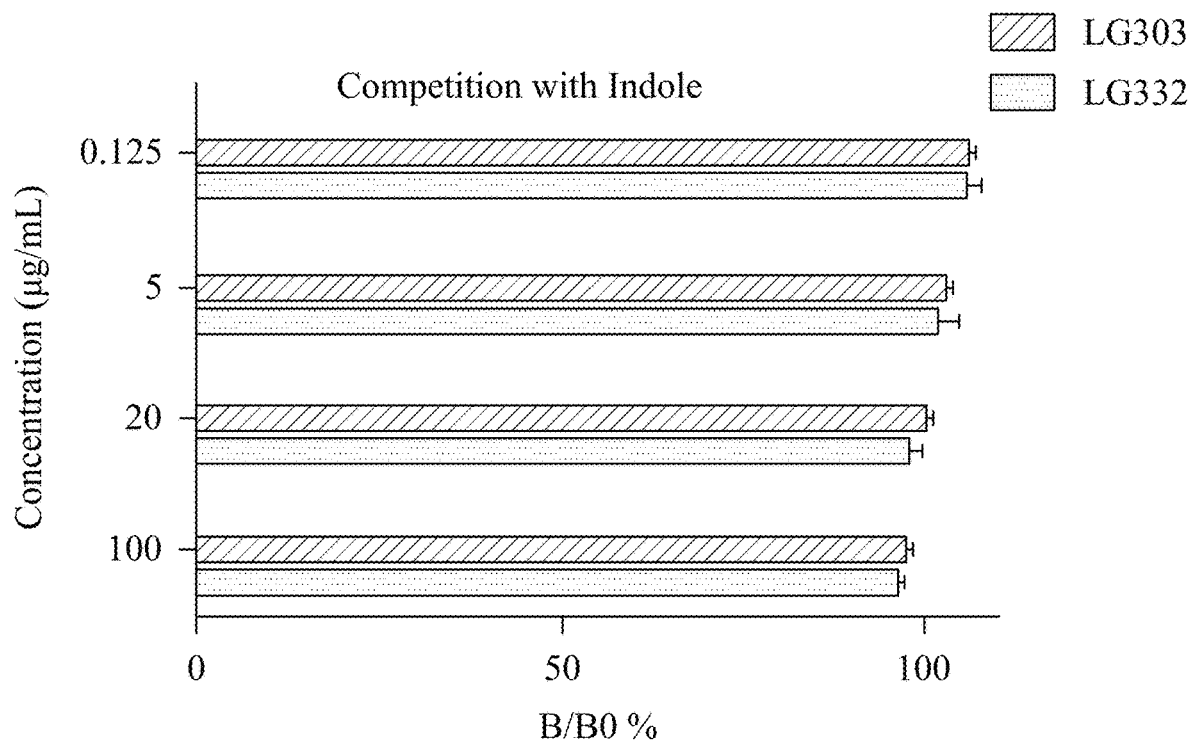
Figure 2D:
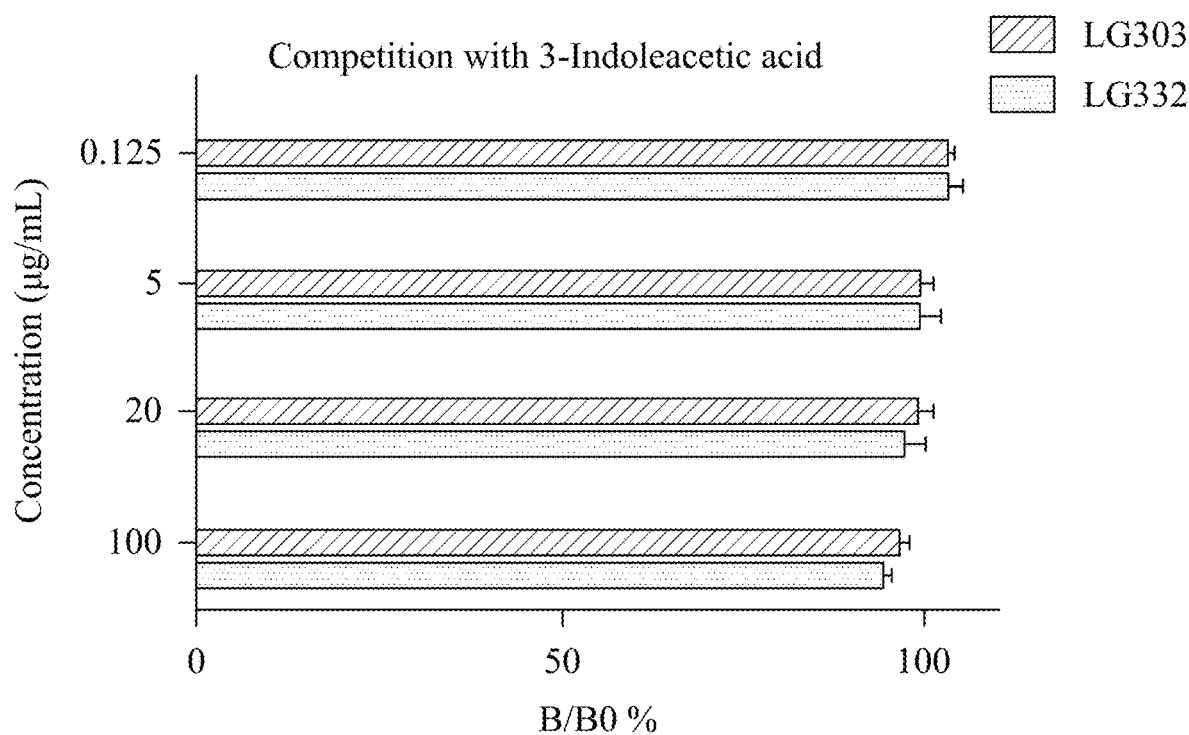

The binding specificity of purified LG303 and LG332 mAbs (100 ng/mL) was reexamined by competitive ELISA that anti-IS mAbs were coated on plates and IS-HRP conjugates served as analytes. Comparative binding activities of LG303 and LG332 under the competing of four compounds at 0.125, 5, 20 and 100 µg/mL concentrations were illustrated in FIGS. 2A (IS), 2B (L-tryptophan), 2C (indole) and 2D (3-indoleacetic acid). The results showed that LG303 and LG332 are highly specific binding to IS with no significant reactivity to L-tryptophan and its other representative biochemical metabolites.

Example 5: Detection of IS in Biological Samples

Figure 3:
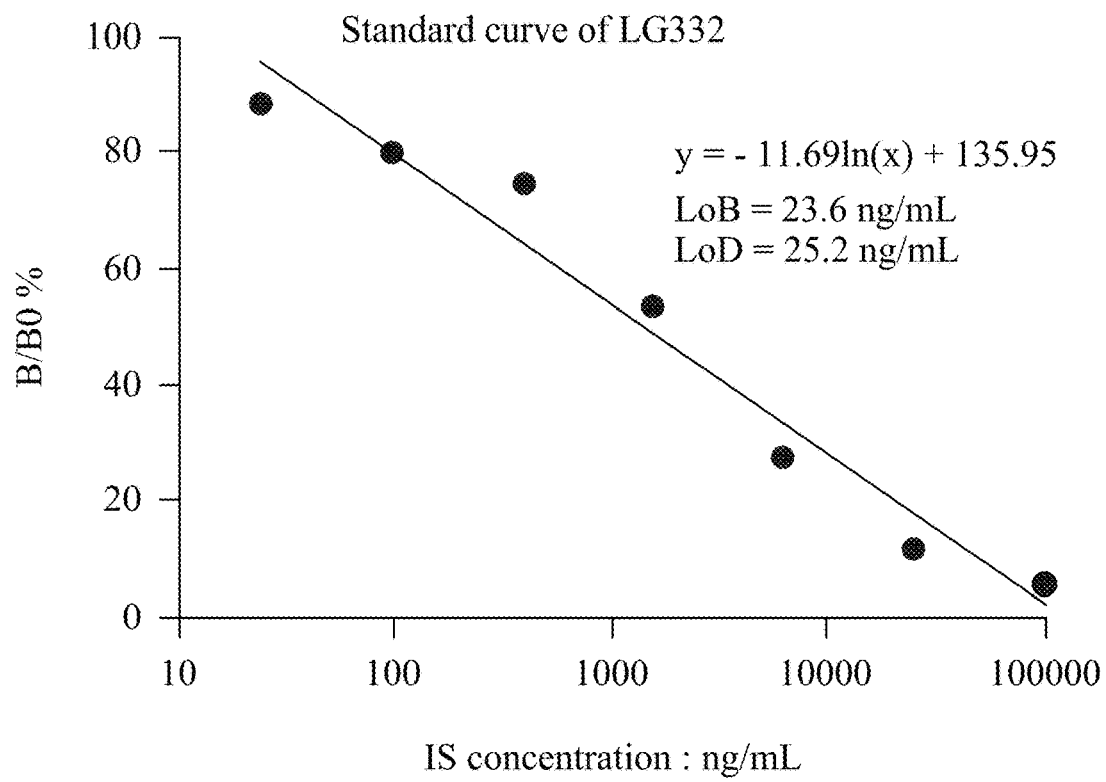
FIG. 3 illustrates a standard curve showing limit of blank (LoB) and limit of detection (LoD) of isolated the anti-IS mAb LG332 in a competition ELISA, in which and LG332 is examined its LoD and LoB under serial concentrations of IS.

To determine whether an isolated anti-IS mAb can detect its antigen target in biological samples, especially with the existence of interfering plasma proteins, thus different concentrations of IS were introduced into human serum and plasma and evaluated by competitive ELISA. Rather, LG332 here was coated onto wells surfaces as the capture antibody. Referring to FIG. 3, it illustrated a standard curve showing the LoB and LoD of LG332 and its LoD was approximately 25.2 ng/mL.

Recovery rates of LG332 in human serum and plasma was shown in Table 1, which states that the binding activity of our anti-IS mAbs was not interfered by human plasma proteins, e.g. albumin, which is regarded to absorb circulating IS in the blood stream.

TABLE 1

Recovery of LG332 in human serum and plasma

| Spiked IS concentrations | LG332 | |
|---|---|---|
| (ng/mL) | Serum | Plasma |
| 50000 | 92.6% | 101.87% |
| 5000 | 102% | 107.5% |
| 500 | 105% | 111% |

Example 6: Removal of IS in Biological Samples

LG303 and LG332 were conjugated to glyoxal agarose gel (BioScience Bead Division of Colloidal Science Solutions, Inc.) column to examine whether they can remove IS from plasma. In this example, IS was spiked into plasma samples from two healthy donors up to a concentration about 40 µg/mL, the LC-MS/MS quantitation of total IS and PCS was serviced by the Department of Laboratory Medicine, Chang Gung Memorial Hospital (Taoyuan, Taiwan). Referring to Tables 2 and 3, LG332 showed a better IS removal rate than LG303. Unexpectedly, the concentration of PCS, another important protein-bound uremic toxin, was also reduced after anti-IS mAb treatment. Since PCS and IS compete the same binding site on human serum albumin (18), when most IS bound by serum albumin was displaced by anti-IS mAbs, there possibly an unclear connection between these two deleterious substances remained to be studied.

TABLE 2

Total IS levels in plasma samples.

| | IS concentration | | | |
|---|---|---|---|---|
| | Donor 1 (LG303-agarose) | | Donor 2 (LG332-agarose) | |
| | Spiked with IS | | | |
| | − | + | − | + |
| [IS, untreated] (μg/mL) | 1.33 | 43 | 0.61 | 43.6 |
| [IS, treated] (μg/mL) | 0.41 | 7.61 | 0.18 | 0.97 |
| Removal rate (%) | 69.17% | 82.3% | 70.49% | 97.78% |

TABLE 3

Total PCS levels in plasma samples.

| | PCS concentration | | | |
|---|---|---|---|---|
| | Donor 1 (LG303-agarose) | | Donor 2 (LG332-agarose) | |
| | Spiked with IS | | | |
| | − | + | − | + |
| [IS, untreated] (μg/mL) | 7.69 | 7.61 | 0.98 | 0.97 |
| [IS, treated] (μg/mL) | 3.58 | 1.39 | 0.18 | 0.19 |
| Removal rate (%) | 53.45% | 81.73% | 81.63% | 80.4% |

Example 7: Efficacy of Anti-IS mAbs in the 5/6 Nx Rat Model

As mentioned above, hemodialysis cannot efficiently remove protein-bound uremic toxins. The potential of anti-IS mAbs in therapeutic uses may be investigated in 5/6 Nx rats because many pathophysiological features of this experimental animal model are common to CKD observed in humans. Therefore, they are supposed to be suitable subjects for studying differences such as the effects of anti-IS mAbs on morphology of kidney or other tissue lesions.

Briefly, male Sprague Dawley® rats (body weight ~300 grams) were separated into five groups including the healthy control, 5/6 Nx, 5/6 Nx with control antibody, 5/6 Nx with LG303, 5/6 Nx with LG332. All the experiment was carried out by the Department of Biochemistry and Molecular Biology of National Cheng Kung University (Tainan, Taiwan). All animal groups except the healthy control were given the renal surgery on the week 0 and rested for one week. The left kidney was exposed, and the upper and lower poles were tied with a polyglycolic acid suture line, followed by right nephrectomy. The peritoneum and skin were then sutured, and the animals were returned to their individual cages. Antibodies were intraperitoneally injected according to rat groups at 10 mg antibody per kg body weight once per week during weeks 1 to 5. At the end of the experiments, the animals were euthanized with an overdose of sodium thiopental and perfused via the left ventricle with phosphate-buffered saline (PBS, pH 7.4; 0.1 M), followed by a fixative solution of formaldehyde; the kidney was removed, cleaned of connective tissue and embedded in paraffin. Histological analyses of renal and cardiovascular tissues were serviced by Litzung Biotechnology Inc. (Taipei, Taiwan).

Figure 4:
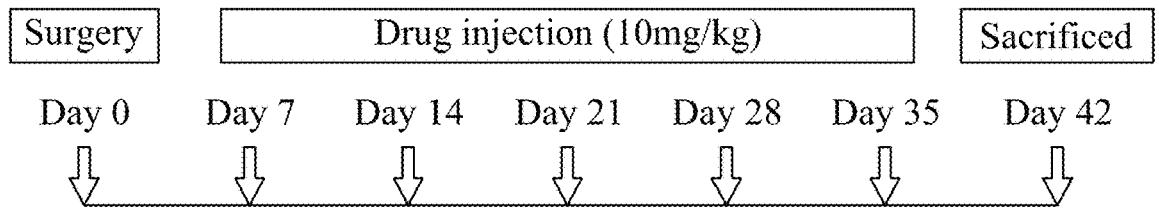
FIG. 4 illustrates a flow chart of experimental strategy on CKD animal model.

Referring to FIG. 4, it illustrates a flowchart of experimental procedures of the animal model according to an embodiment of the present invention. As shown in FIG. 4, rats underwent 5/6 Nx or a sham control. Rats were given one week of rest followed by injections of control mouse IgG, LG303, and LG332 as described previously. On the day 42 (the 6th week), rats were sacrificed and tissue biopsy specimen of interests were collected for analyses.

Figure 5A:
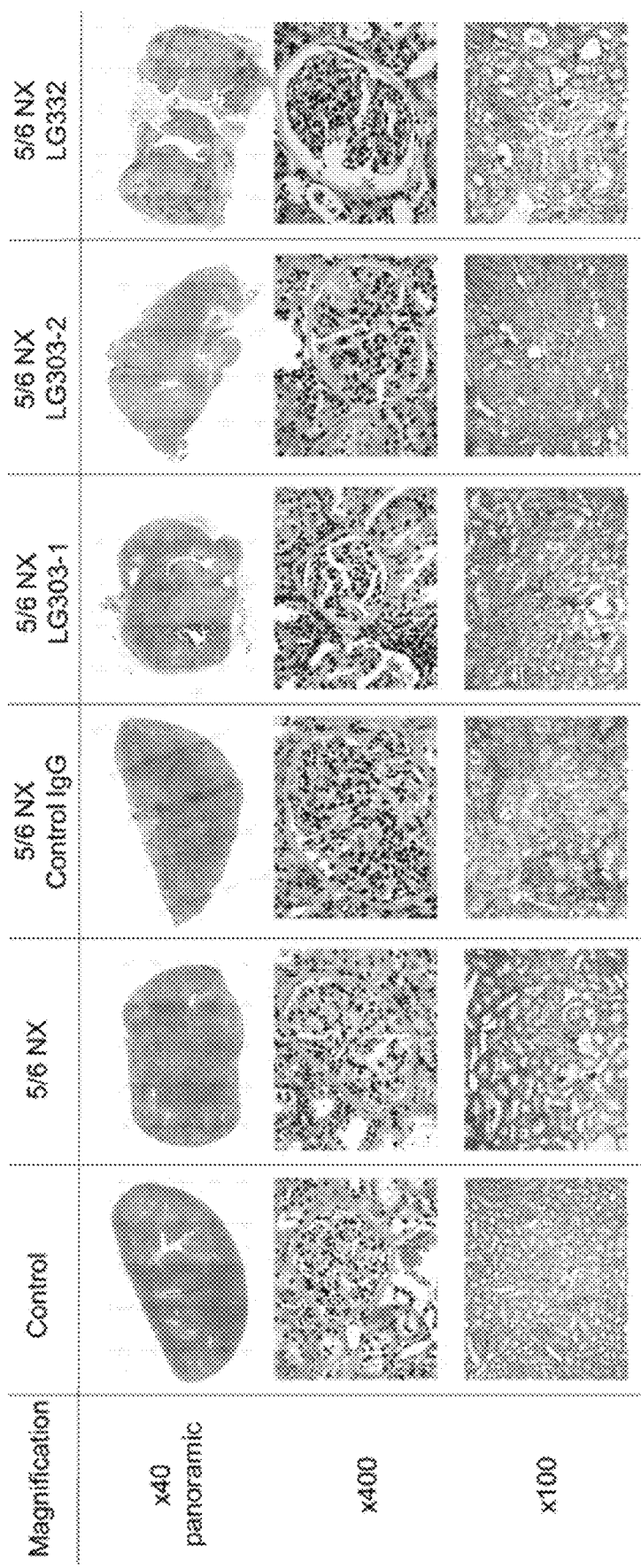
FIGS. 5A to 5B illustrate hematoxylin and eosin (H&E)-stained histological images of kidney (FIG. 5A) and heart (FIG. 5B) sections of test animals.
Figure 5B:
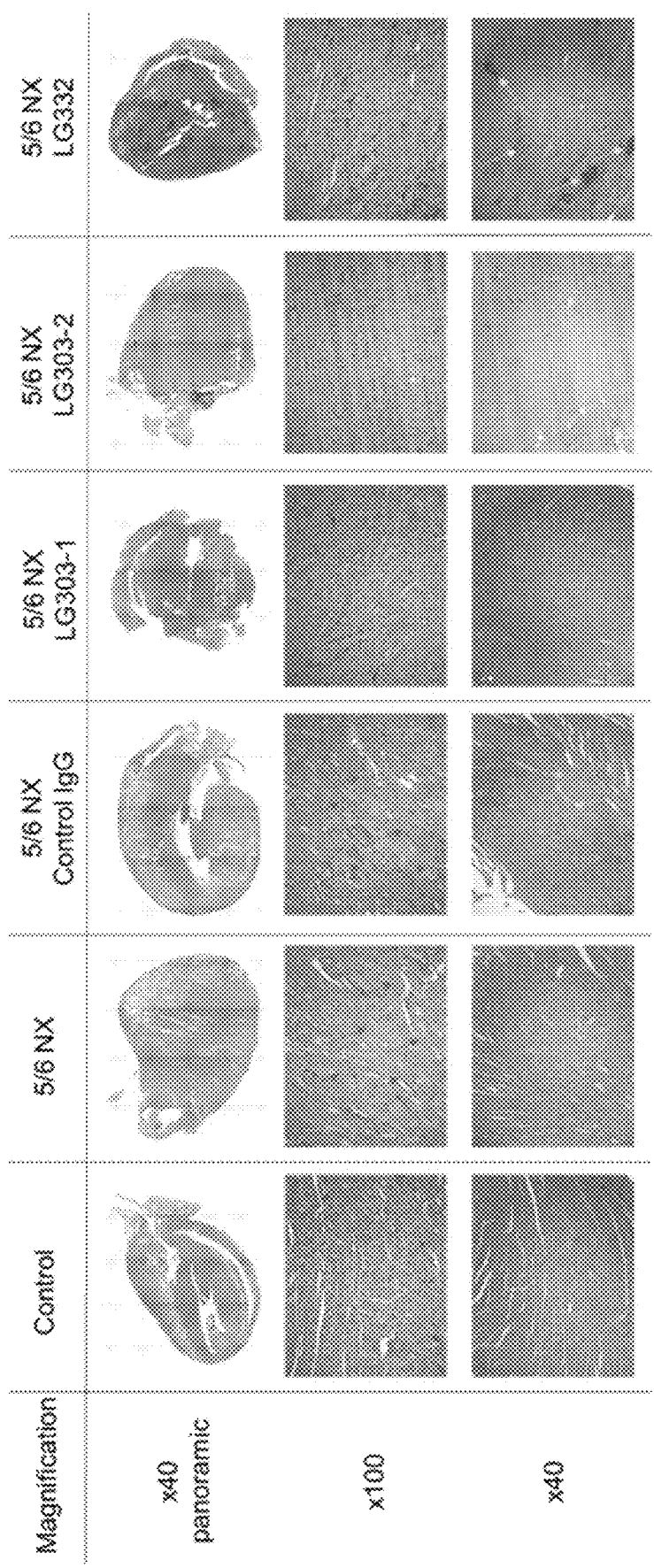

Referring to FIGS. 5A to 5B, they illustrated hematoxylin and eosin (H&E)-stained kidney (FIG. 5A) and heart (FIG. 5B) sections of test animals. In FIG. 5A, the yellow arrow indicated glomerular sclerosis, the red arrow indicated tubular vacuoles, the light blue arrow indicated interstitial fibrosis and the green arrow indicated pro-inflammatory cell infiltration. In FIG. 5B, the green arrow indicated rearrangement of cardiomyocytes and the yellow arrow indicated infiltration of immune cells. In the histological results of FIGS. 5A to 5B, it was found that the experimental group treated with LG303 showed less pathological change than other experimental groups. As shown in FIG. 5A, 5/6 Nx rats had glomerular sclerosis, expanded tubular vacuoles, interstitial fibrosis, and immune cells infiltration. Under rats treated with control IgG and LG332, the phenomena were similar with 5/6 Nx rats. Interestingly, it was found that LG303 could be beneficial to 5/6 Nx rats. Herein, it was found that pro-inflammatory cells infiltration and other pathological changes were decreased dramatically. Moreover, after LG303 treatment, cardiac rearrangement was reduced as compared with control IgG and LG332 (as shown in FIG. 5B).

Figure 6:
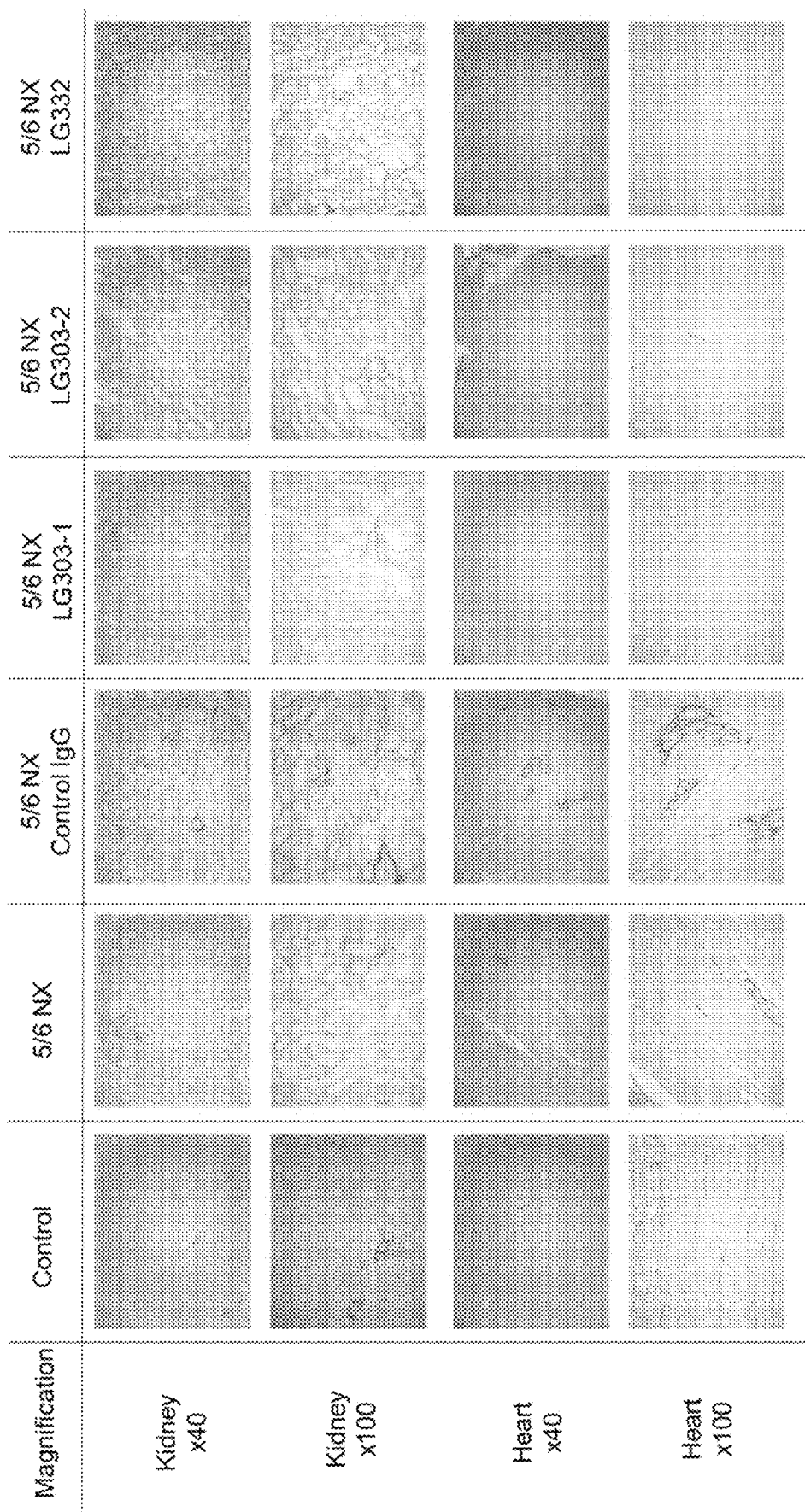
FIG. 6 illustrates Sirius red-stained histological images of kidney and heart sections of test animals for detecting collagen.
Figure 7:
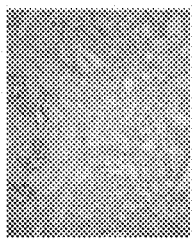
FIG. 7 illustrates immunohistochemistry (INC) images of kidney and heart sections of test animals using collagen type IV antibody.
Figure 8:
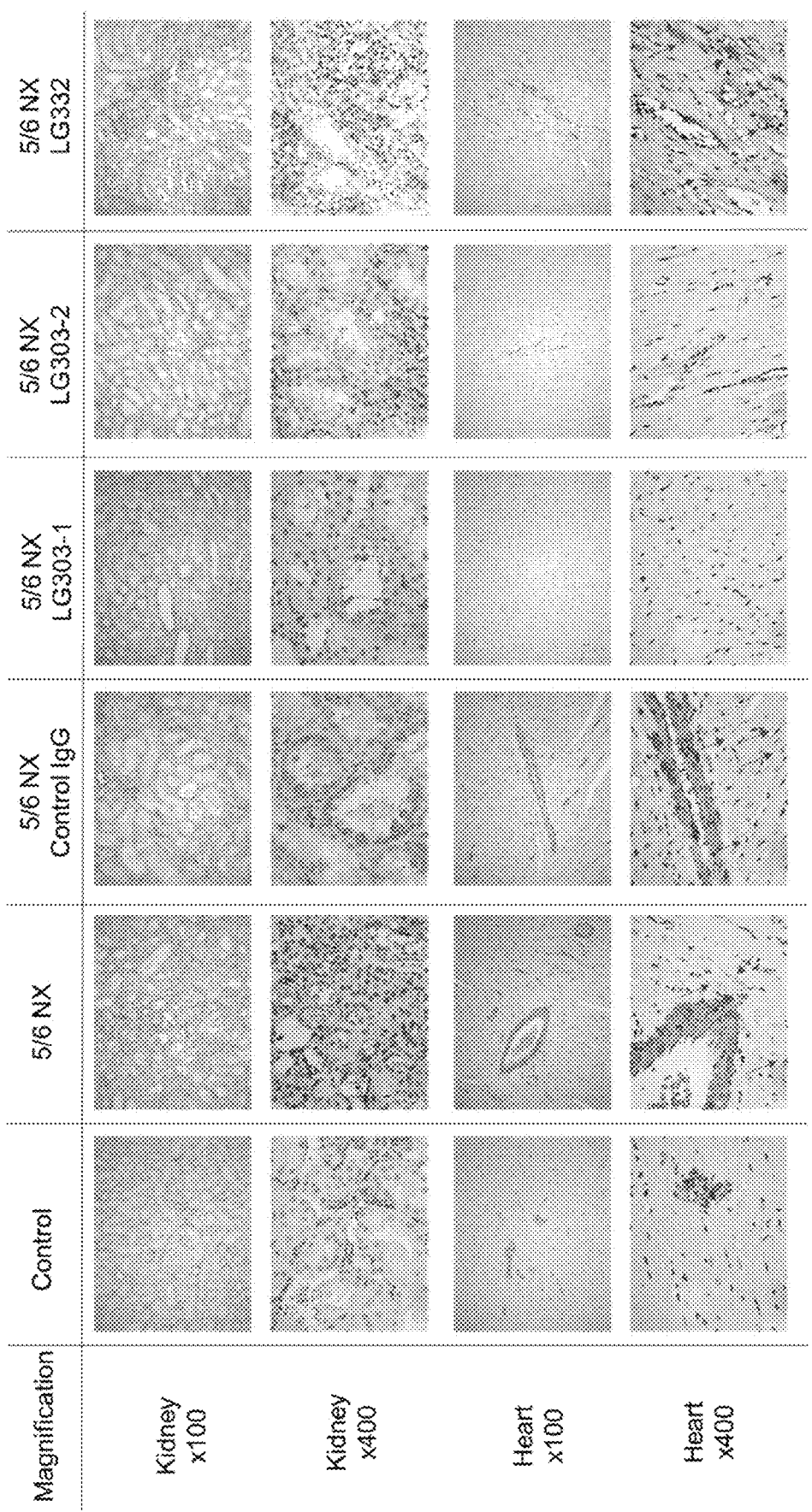
FIG. 8 illustrates IHC images of kidney and heart sections of test animals using a-smooth muscle actin (a-SMA) antibody for detecting fibrosis increasing region.

To further identify anti-fibrotic effects of LG303 in 5/6 Nx rats, the biopsy specimens of these heart and kidney tissues were stained by Sirius red. Referring to FIG. 6, it illustrated Sirius red-stained kidney and heart sections of test animals for observing collagen expression patterns. Referring to FIG. 7, it illustrated by IHC images of kidney and heart sections of test animals using collagen type IV antibody, in which rats' kidney and heart sections were performed IHC with collagen IV antibody for specific collagen observation. Compared to animal groups given with control antibodies and healthy sham, FIG. 6 and FIG. 7 suggested that rats subjected to an anti-IS mAb treatment showed a trend to a lowered expression of ECM protein type I and collagen IV collagens. FIG. 8 illustrated IHC images of kidney and heart sections of test animals using α-SMA antibody for identifying transdifferentiation of fibroblasts into myofibroblasts (dark brown areas indicated by red arrows). As shown in FIG. 8, the expression of a-SMA was obviously reduced by anti-IS mAbs, whereas the performance of LG303 was better than that of LG332. This superiority of LG303 over LG332 was in agreement with the inhibiting activities of excess collagen deposition visualized in FIG. 6 and FIG. 7.

Figure 9:
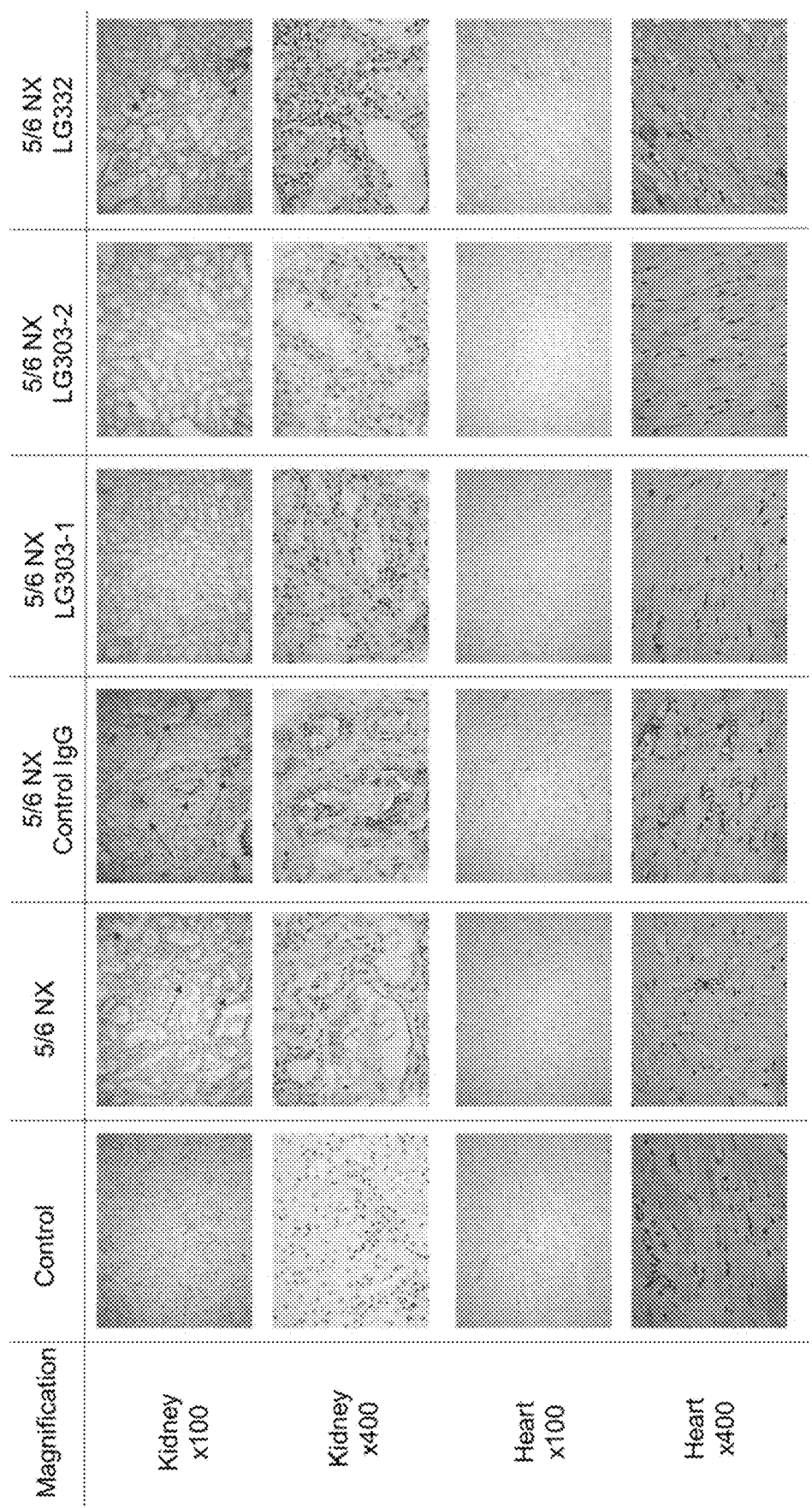
FIG. 9 illustrates IHC images of kidney and heart sections of test animals using M30 antibody for detecting cell apoptosis events.

FIG. 9 illustrated the histopathological view of kidney and heart lesions caused by renal injury in test animals using M30 antibody for detecting apoptotic events (indicated by red arrows). According to the M30 immunostaining, apoptotic cell death was identified only in sections from kidney rather than heart, and anti-IS mAbs prevented unscheduled apoptosis onset in glomerular cells, especially epithelial cells. Once such mAbs applied in clinical, renal functions of CKD patients could be reserved or rescued.

In conclusion, above experimental results supported that an administration of isolated anti-IS mAb exert significant anti-fibrotic and anti-apoptotic effects on cells of kidney and heart in the chosen animal model for CKD. Moreover, these results are promising and indicate that neutralizing IS by specific mAbs might alleviate IS-related pathological symptoms.

Although the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, the spirit and claim scope should not be limited to the description of the exemplified embodiments demonstrated above.

REFERENCES

1. Meyer, T. W., and T. H. Hostetter. 2007. Uremia. *N. Engl. J. Med.* 357: 1316-1325.
2. Vanholder, R., R. De Smet, and N. Lameire. 2001. Protein-bound uremic solutes: the forgotten toxins. *Kidney Int. Suppl.* 78: S266-270.
3. Lee, C.-T., C.-C. Kuo, Y.-M. Chen, C.-Y. Hsu, W.-C. Lee, Y.-C. Tsai, H.-Y. Ng, L.-C. Kuo, T. T.-Y. Chiou, Y.-K. Yang, B.-C. Cheng, and J.-B. Chen. 2010. Factors associated with blood concentrations of indoxyl sulfate and p-cresol in patients undergoing peritoneal dialysis. *Perit. Dial. Int. J. Int. Soc. Pent. Dial.* 30: 456-463.
4. Wu, I.-W., K.-H. Hsu, C.-C. Lee, C.-Y. Sun, H.-J. Hsu, C.-J. Tsai, C.-Y. Tzen, Y.-C. Wang, C.-Y. Lin, and M.-S. Wu. 2011. p-Cresyl sulphate and indoxyl sulphate predict progression of chronic kidney disease. *Nephrol. Dial. Transplant. Off. Publ. Eur. Dial. Transpl. Assoc.—Eur. Ren. Assoc.* 26: 938-947.
5. Schulman, G., T. Berl, G. J. Beck, G. Remuzzi, E. Ritz, K. Arita, A. Kato, and M. Shimizu. 2015. Randomized Placebo-Controlled EPPIC Trials of AST-120 in CKD. *J. Am. Soc. Nephrol. JASN* 26: 1732-1746.
6. Yamaguchi, J., T. Tanaka, and R. Inagi. 2017. Effect of AST-120 in Chronic Kidney Disease Treatment: Still a Controversy? *Nephron* 135: 201-206.
7. Lin, C.-N., I.-W. Wu, Y.-F. Huang, S.-Y. Peng, Y.-C. Huang, and H.-C. Ning. 2018. Measuring serum total and free indoxyl sulfate and p-cresyl sulfate in chronic kidney disease using UPLC-MS/MS. *J. Food Drug Anal.*
8. Al Za'abi, M., B. Ali, and M. Al Toubi. 2013. HPLC-fluorescence method for measurement of the uremic toxin indoxyl sulfate in plasma. *J. Chromatogr. Sci.* 51: 40-43.
9. Hoshi, H., K. Kikuchi, Y. Itoh, and A. Konagai. 2015. Indoxyl sulfate measurement method. US20150355171A1
10. Taki, K., S. Nakamura, M. Miglinas, A. Enomoto, and T. Niwa. 2006. Accumulation of indoxyl sulfate in OAT1/3-positive tubular cells in kidneys of patients with chronic renal failure. *J. Ren. Nutr. Off. J. Counc. Ren. Nutr. Natl. Kidney Found.* 16: 199-203.
11. Ito, S., M. Osaka, T. Edamatsu, Y. Itoh, and M. Yoshida. 2016. Crucial Role of the Aryl Hydrocarbon Receptor (AhR) in Indoxyl Sulfate-Induced Vascular Inflammation. *J. Atheroscler. Thromb.* 23: 960-975.
12. Essono, S., Y. Frobert, J. Grassi, C. Créminon, and D. Boquet. 2003. A general method allowing the design of oligonucleotide primers to amplify the variable regions from immunoglobulin cDNA. *J. Immunol. Methods* 279: 251-266.
13. McCafferty, J., A. D. Griffiths, G. Winter, and D. J. Chiswell. 1990. Phage antibodies: filamentous phage displaying antibody variable domains. *Nature* 348: 552-554.
14. Dai, C., L. P. Kiss, and Y. Liu. 2008. Animal Models of Kidney Diseases. In *Sourcebook of Models for Biomedical Research* P. M. Conn, ed. Humana Press, Totowa, N.J. 657-664.
15. Yang, H.-C., Y. Zuo, and A. B. Fogo. 2010. Models of chronic kidney disease. *Drug Discov. Today Dis. Models* 7: 13-19.
16. Nangaku, M. 2004. Mechanisms of tubulointerstitial injury in the kidney: final common pathways to end-stage renal failure. *Intern. Med. Tokyo Jpn.* 43: 9-17.
17. Miwa, A., M. Yoshioka, A. Shirahata, and Z. Tamura. 1977. Preparation of specific antibodies to catecholamines and L-3,4-dihydroxyphenylalanine. I. Preparation of the conjugates. *Chem. Pharm. Bull.* (Tokyo) 25: 1904-1910.
18. Watanabe, H., T. Noguchi, Y. Miyamoto, D. Kadowaki, S. Kotani, M. Nakajima, S. Miyamura, Y. Ishima, M. Otagiri, and T. Maruyama. 2012. Interaction between two sulfate-conjugated uremic toxins, p-cresyl sulfate and indoxyl sulfate, during binding with human serum albumin. *Drug Metab. Dispos. Biol. Fate Chem.* 40: 1423-1428.

What is claimed is:

1. An isolated monoclonal antibody or antigen-binding fragment thereof, comprising:
a heavy chain variable (VH) domain of SEQ ID NO: 4 or 14, comprising complementarity-determining regions (CDR)-H1, CDR-H2 and CDR-H3; and
a light chain variable (VL) domain of SEQ ID NO: 9 or 19, comprising variable regions CDR-L1, CDR-L2 and CDR-L3, and
wherein amino acid sequences of CDRs are set forth below:
CDR-H1 selected from any one of SEQ ID NOs: 1 or 11;
CDR-H2 selected from any one of SEQ ID NOs: 2 or 12;
CDR-H3 selected from any one of SEQ ID NOs: 3 or 13;
CDR-L1 selected from any one of SEQ ID NOs: 6 or 16;
CDR-L2 selected from any one of SEQ ID NOs: 7 or 17; and
CDR-L3 selected from any one of SEQ ID NOs: 8 or 18.

2. The isolated monoclonal antibody or antigen-binding fragment thereof according to claim 1, wherein the isolated antibody and/or fragment thereof is a full-length immunoglobulin molecule, a single-chain variable fragment (scFv), a variable fragment (Fv), a Fab fragment, a Fab' fragment, a single domain antibody (dAb), a multispecific binding molecule or any combination of an isolated human, chimeric, humanized, synthetic, recombinant antibody or an antigen-binding fragment thereof.

3. The isolated monoclonal antibody or antigen-binding fragment thereof according to claim 1, wherein the isolated monoclonal antibody or fragment thereof is screened from an in-vitro surface display system.

4. The isolated monoclonal antibody or antigen-binding fragment thereof according to claim 1, wherein the isolated antibody or fragment thereof is chemically modified or mixed with a pharmaceutically acceptable carrier.

5. A device composition for removing indoxyl sulfate, comprising the isolated monoclonal antibody or antigen-binding fragment thereof according to claim 1.

6. The device composition for removing indoxyl sulfate according to claim 5, wherein the isolated monoclonal antibody or antigen-binding fragment thereof is conjugated to a solid phase.

7. A pharmaceutical composition for removing or reducing indoxyl sulfate in a subject, comprising the isolated monoclonal antibody or antigen-binding fragment thereof according to claim 1.

8. The pharmaceutical composition for removing or reducing indoxyl sulfate in the subject according to claim 7, further comprising a medical adsorbent.

9. The pharmaceutical composition for removing or reducing indoxyl sulfate in the subject according to claim 8, wherein the medical adsorbent includes an activated carbon absorbent.

* * * * *

SEQUENCE LISTING

```
<160> NUMBER OF SEQ ID NOS: 21

<210> SEQ ID NO 1
<211> LENGTH: 8
<212> TYPE: PRT
<213> ORGANISM: Artificial sequence
<220> FEATURE:
<223> OTHER INFORMATION: CDR-H1 of LG303

<400> SEQUENCE: 1

Gly Phe Asn Ile Lys Asp Thr Tyr
                5

<210> SEQ ID NO 2
<211> LENGTH: 8
<212> TYPE: PRT
<213> ORGANISM: Artificial sequence
<220> FEATURE:
```

<223> OTHER INFORMATION: CDR-H2 of LG303

<400> SEQUENCE: 2

Ile Asp Pro Ala Asn Gly Asp Thr
                5

<210> SEQ ID NO 3
<211> LENGTH: 13
<212> TYPE: PRT
<213> ORGANISM: Artificial sequence
<220> FEATURE:
<223> OTHER INFORMATION: CDR-H3 of LG303

<400> SEQUENCE: 3

Thr Arg Arg Pro Leu Tyr Gly Arg Ser Ser Phe Asp Phe
                5                   10

<210> SEQ ID NO 4
<211> LENGTH: 120
<212> TYPE: PRT
<213> ORGANISM: Artificial sequence
<220> FEATURE:
<223> OTHER INFORMATION: V_region of heavy chain of LG303

<400> SEQUENCE: 4

Glu Val Gln Leu Gln Gln Ser Gly Thr Asp Leu Val Lys Pro Gly Ala
  1               5                  10                  15

Ser Val Lys Leu Ser Cys Arg Ala Ser Gly Phe Asn Ile Lys Asp Thr
             20                  25                  30

Tyr Met His Trp Val Lys Gln Arg Pro Glu Gln Gly Leu Gln Trp Ile
         35                  40                  45

Gly Arg Ile Asp Pro Ala Asn Gly Asp Thr Lys Tyr Asp Pro Lys Phe
     50                  55                  60

Gln Gly Lys Ala Ala Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Thr Arg Arg Pro Leu Tyr Gly Arg Ser Ser Phe Asp Phe Trp Gly Gln
            100                 105                 110

Gly Thr Thr Leu Thr Val Ser Ser
        115                 120

<210> SEQ ID NO 5
<211> LENGTH: 360
<212> TYPE: DNA
<213> ORGANISM: Artificial sequence
<220> FEATURE:
<223> OTHER INFORMATION: V_region of heavy chain of LG303

<400> SEQUENCE: 5
gaggttcagc tgcagcagtc tgggacagac cttgtgaagc caggggcctc agtcaagttg      60
tcctgcagag cttctggctt caacattaaa gacacctata tgcactgggt taagcagagg     120
cctgaacagg gcctgcagtg gattggaagg attgatcctg cgaatggtga ctaaaatat      180 gacccgaagt tccagggcaa ggccgctata acagcagaca tcctccaa cacagcctac       240 ctgcagctca gcagcctgac atctgaggac actgccgtct attactgtac tagacgaccc     300
ctctacggtc gtagctcttt tgacttctgg ggccaaggca ccactctcac agtctcctca     360

<210> SEQ ID NO 6
<211> LENGTH: 6

<212> TYPE: PRT
<213> ORGANISM: Artificial sequence
<220> FEATURE:
<223> OTHER INFORMATION: CDR-L1 of LG303

<400> SEQUENCE: 6

Gln Ser Ile Gly Thr Asn
                5

<210> SEQ ID NO 7
<211> LENGTH: 3
<212> TYPE: PRT
<213> ORGANISM: Artificial sequence
<220> FEATURE:
<223> OTHER INFORMATION: CDR-L2 of LG303

<400> SEQUENCE: 7

Tyr Ala Ser

<210> SEQ ID NO 8
<211> LENGTH: 9
<212> TYPE: PRT
<213> ORGANISM: Artificial sequence
<220> FEATURE:
<223> OTHER INFORMATION: CDR-L3 of LG303

<400> SEQUENCE: 8

Gln Gln Gly Asn Ser Trp Pro Leu Thr
                5

<210> SEQ ID NO 9
<211> LENGTH: 107
<212> TYPE: PRT
<213> ORGANISM: Artificial sequence
<220> FEATURE:
<223> OTHER INFORMATION: V_region of light chain of LG303

<400> SEQUENCE: 9

Asp Ile Leu Leu Thr Gln Ser Pro Ala Ile Leu Ser Val Ser Pro Gly
                5                  10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Leu Asn Ser Val Glu Ser
65                  70                  75                  80

Glu Asp Ile Ala Asp Tyr Tyr Cys Gln Gln Gly Asn Ser Trp Pro Leu
                85                  90                  95

Thr Phe Gly Ala Gly Thr Lys Leu Glu Ile Lys
            100                 105

<210> SEQ ID NO 10
<211> LENGTH: 324
<212> TYPE: DNA
<213> ORGANISM: Artificial sequence
<220> FEATURE:
<223> OTHER INFORMATION: V_region of light chain of LG303

<400> SEQUENCE: 10
gatattttgc tgactcagtc tccagccatc ctgtctgtga gtccaggaga aagagtcagt      60
ttctcctgca gggccagtca gagcattggc acaaacatac actggtatca gcaaagaaca     120

```
aatggttctc caaggcttct cataaagtat gcttctgagt ctatctctgg gatcccttcc    180
aggtttagtg gcagtggatc agggacagat tttactctta gcctcaacag tgtggagtct    240
gaagatattg cagattatta ctgtcaacaa ggtaatagct ggccgctcac gttcggtgct    300
gggaccaaac tggaaataaa acgt                                           324
```

<210> SEQ ID NO 11
<211> LENGTH: 8
<212> TYPE: PRT
<213> ORGANISM: Artificial sequence
<220> FEATURE:
<223> OTHER INFORMATION: CDR-H1 of LG332

<400> SEQUENCE: 11

Gly Phe Asn Ile Lys Asp Ala Tyr
                5

<210> SEQ ID NO 12
<211> LENGTH: 8
<212> TYPE: PRT
<213> ORGANISM: Artificial sequence
<220> FEATURE:
<223> OTHER INFORMATION: CDR-H2 of LG332

<400> SEQUENCE: 12

Ile Ala Pro Ala Asn Gly Asn Ile
                5

<210> SEQ ID NO 13
<211> LENGTH: 14
<212> TYPE: PRT
<213> ORGANISM: Artificial sequence
<220> FEATURE:
<223> OTHER INFORMATION: CDR-H3 of LG332

<400> SEQUENCE: 13

Ala Arg Arg Pro Leu Tyr Gly Tyr Val Glu Tyr Phe Asp Val
                5                   10

<210> SEQ ID NO 14
<211> LENGTH: 121
<212> TYPE: PRT
<213> ORGANISM: Artificial sequence
<220> FEATURE:
<223> OTHER INFORMATION: V_region of heavy chain of LG332

<400> SEQUENCE: 14

Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Ala
            20                  25                  30

Tyr Met His Trp Val Lys Gln Arg Pro Glu Gln Gly Leu Glu Trp Ile
        35                  40                  45

Gly Arg Ile Ala Pro Ala Asn Gly Asn Ile Lys Tyr Asp Pro Thr Phe
    50                  55                  60

Gln Gly Lys Ala Thr Ile Thr Ala Asp Thr Ser Ser Asn Thr Ala Tyr
65                  70                  75                  80

Val Gln Leu Ser Ser Leu Thr Ser Glu Asp Thr Ala Val Tyr Tyr Cys
                85                  90                  95

Ala Arg Arg Pro Leu Tyr Gly Tyr Val Glu Tyr Phe Asp Val Trp Gly
            100                 105                 110

Ala Gly Thr Thr Val Thr Val Ser Ser
        115                 120

<210> SEQ ID NO 15
<211> LENGTH: 363
<212> TYPE: DNA
<213> ORGANISM: Artificial sequence
<220> FEATURE:
<223> OTHER INFORMATION: V_region of heavy chain of LG332

<400> SEQUENCE: 15
gaggttcagc ttcagcagtc tggggcagag cttgtgaagc caggggcctc agtcaagttg      60
tcctgcacag cttctggctt caacattaaa gacgcctata tgcactgggt gaagcagagg     120
cctgaacagg gcctggagtg gattggaagg attgctcctg cgaatggtaa tattaaatat     180
gacccgacgt tccagggcaa ggccactata acagctgaca catcctccaa cacagcctac     240
gtgcagctca gcagcctgac atctgaggac actgccgtct attactgtgc tagaagaccc     300
ctctacggct acgttgagta cttcgatgtc tggggcgctg ggaccacggt caccgtctcc     360
tca                                                                   363

<210> SEQ ID NO 16
<211> LENGTH: 6
<212> TYPE: PRT
<213> ORGANISM: Artificial sequence
<220> FEATURE:
<223> OTHER INFORMATION: CDR-L1 of LG332

<400> SEQUENCE: 16

Gln Asn Val Arg Thr Ala
                5

<210> SEQ ID NO 17
<211> LENGTH: 3
<212> TYPE: PRT
<213> ORGANISM: Artificial sequence
<220> FEATURE:
<223> OTHER INFORMATION: CDR-L2 of LG332

<400> SEQUENCE: 17

Leu Ala Ser

<210> SEQ ID NO 18
<211> LENGTH: 9
<212> TYPE: PRT
<213> ORGANISM: Artificial sequence
<220> FEATURE:
<223> OTHER INFORMATION: CDR-L3 of LG332

<400> SEQUENCE: 18

Leu Gln His Trp Asn Phe Pro Leu Thr
                5

<210> SEQ ID NO 19
<211> LENGTH: 107
<212> TYPE: PRT
<213> ORGANISM: Artificial sequence
<220> FEATURE:
<223> OTHER INFORMATION: V_region of light chain of LG332

<400> SEQUENCE: 19

Asp Ile Val Met Thr Gln Ser Gln Lys Phe Met Ser Thr Ser Val Gly
                5                  10                  15

Asp Arg Val Ser Ile Thr Cys Lys Ala Ser Gln Asn Val Arg Thr Ala

```
                      20                  25                  30
Val Gly Trp Tyr Gln Gln Lys Pro Gly Gln Ser Pro Lys Thr Leu Ile
            35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Phe Pro Leu
                85                  90                  95

Thr Phe Gly Gly Gly Thr Lys Leu Glu Ile Arg
            100                 105

<210> SEQ ID NO 20
<211> LENGTH: 323
<212> TYPE: DNA
<213> ORGANISM: Artificial sequence
<220> FEATURE:
<223> OTHER INFORMATION: V_region of light chain of LG332

<400> SEQUENCE: 20
gacattgtga tgacccagtc tcaaaaattc atgtccacat cagtaggaga cagggtcagc      60
atcacctgca aggccagtca gaatgttcgt actgctgtag gctggtatca acagaaacca     120
gggcagtctc ctaaaacact gatttacttg gcatccaacc ggcacactgg agtccctgat     180
cgcttcacag gcagtggatc tgggacagat ttcactctca ccattagtaa tgtgcaatct     240
gaagacctgg cagattattt ctgtctgcaa cattggaatt ttcctctgac gttcggtgga     300
ggcaccaagc tggagatcag acg                                             323

<210> SEQ ID NO 21
<211> LENGTH: 15
<212> TYPE: PRT
<213> ORGANISM: Artificial sequence
<220> FEATURE:
<223> OTHER INFORMATION: linker

<400> SEQUENCE: 21

Gly Gly Gly Gly Ser Gly Gly Gly Gly Ser Gly Gly Gly Gly Ser
                5                   10                  15
```